United States Patent
Oud

(10) Patent No.: US 11,926,582 B2
(45) Date of Patent: Mar. 12, 2024

(54) ULTRA-LOW EMISSION ETHYLENE PLANT

(71) Applicant: TECHNIP ENERGIES FRANCE SAS, Nanterre (FR)

(72) Inventor: Peter Oud, Zoetermeer (NL)

(73) Assignee: TECHNIP ENERGIES FRANCE, Nanterre (FR)

( * ) Notice: Subject to any disclaimer, the term of this patent is extended or adjusted under 35 U.S.C. 154(b) by 0 days.

(21) Appl. No.: 17/917,921

(22) PCT Filed: Apr. 9, 2021

(86) PCT No.: PCT/EP2021/059324
§ 371 (c)(1),
(2) Date: Oct. 7, 2022

(87) PCT Pub. No.: WO2021/205011
PCT Pub. Date: Oct. 14, 2021

(65) Prior Publication Data
US 2023/0135324 A1 May 4, 2023

(30) Foreign Application Priority Data
Apr. 9, 2020 (EP) .................... 20169114

(51) Int. Cl.
*C07C 4/04* (2006.01)
*B01J 6/00* (2006.01)
(Continued)

(52) U.S. Cl.
CPC .................. *C07C 4/04* (2013.01); *B01J 6/00* (2013.01); *C07C 11/04* (2013.01); *F01K 13/00* (2013.01); *C25B 1/04* (2013.01)

(58) Field of Classification Search
CPC .... C07C 4/04; C07C 11/04; B01J 6/00; F01K 13/00; C25B 1/04
See application file for complete search history.

(56) References Cited

U.S. PATENT DOCUMENTS

| 4,479,869 A | 10/1984 | Petterson et al. |
| 9,334,204 B1 * | 5/2016 | Radaelli .................. B01J 8/001 |

(Continued)

FOREIGN PATENT DOCUMENTS

| EP | 3748138 A1 | 12/2020 |
| GB | 1533163 A | 11/1978 |

(Continued)

OTHER PUBLICATIONS

PCT International Search Report and Written Opinion dated May 6, 2021, issued during the prosecution of corresponding PCT International Patent Application No. PCT/US2021/059324.

*Primary Examiner* — Audrey B. Walter
(74) *Attorney, Agent, or Firm* — Locke Lord LLP; Gabrielle L. Gelozin; Christopher J. Capelli

(57) ABSTRACT

An ethylene plant including a cracking furnace for converting a hydrocarbon feedstock into a cracked gas stream, and a separation section to provide at least an ethylene-enriched product stream, a hydrogen-enriched fuel stream and a methane-enriched fuel stream from the cracked gas stream. A passage way is provided for feeding at least part of the hydrogen-enriched fuel from the separation section to a burner of the cracking furnace and/or a passage way for feeding at least part of the hydrogen-enriched fuel from the separation section to a burner of a waste heat recovery boiler of a combined cycle gas turbine power plant (CCGT). The CCGT includes a gas turbine, which CCGT is configured to generate electric power and/or to generate high pressure steam to drive a steam turbine forming part of a steam generation circuit of the ethylene plant.

30 Claims, 11 Drawing Sheets

(51) Int. Cl.
*C07C 11/04* (2006.01)
*C25B 1/04* (2021.01)
*F01K 13/00* (2006.01)

(56) References Cited

U.S. PATENT DOCUMENTS

2005/0089299 A1    4/2005  Woodfin
2006/0116543 A1    6/2006  Bellet et al.

FOREIGN PATENT DOCUMENTS

WO    2018/229267 A1    6/2018
WO    2019036426 A1    2/2019

* cited by examiner

ULTRA-LOW EMISSION ETHYLENE PLANT

CROSS-REFERENCE TO RELATED APPLICATIONS

This application is a U.S. National Stage filed under 35 U.S.C. § 371, based on International PCT Application No. PCT/EP2021/059324, filed on Apr. 9, 2021, which claims priority to European Application EP20169114.4 filed on Apr. 9, 2020 in the European Patent Office. The entire contents of these applications are incorporated herein by reference in their entirety.

The present invention relates to an ethylene plant and to a process for producing ethylene in such plant. The invention further relates to a method for the temporary storage of renewable power using the ethylene plant and to a method for indirect conversion of hydrogen to methane-rich gas using the ethylene plant.

A conventional cracking furnace system, as is for example disclosed in document U.S. Pat. No. 4,479,869, generally comprises a convection section, in which hydrocarbon feedstock is preheated and/or partly evaporated and mixed with dilution steam to provide a feedstock-dilution steam mixture. The system also comprises a radiant section, including at least one radiant coil in a firebox, in which the feedstock-dilution steam mixture from the convection section is converted into product and by-product components at high temperature by pyrolysis. The system further comprises a cooling section including at least one quench exchanger, for example a transfer line exchanger, configured to quickly quench the product or cracked gas leaving the radiant section in order to stop pyrolysis side reactions, and to preserve the equilibrium of the reactions in favor of the products. Heat from the transfer line exchanger can be recovered in the form of high pressure steam.

A drawback of such conventional systems is that a lot of fuel needs to be supplied for the pyrolysis reaction. In order to reduce this fuel consumption, the firebox efficiency, the percentage of the released heat in the firebox that is absorbed by the radiant coil, can be significantly increased. However, the heat recovery scheme in the convection section of a conventional cracking furnace system with increased firebox efficiency has only limited capabilities to heat up the hydrocarbon feedstock to reach the optimum temperature to enter the radiant section. As a result, reducing fuel consumption, and thus reducing $CO_2$ emission, is hardly possible within a conventional cracking furnace system.

WO2018/229267 addresses this problem and significantly improves the firebox efficiency of cracking furnaces and reduces $CO_2$ emissions from the cracking furnaces. However, such a high efficiency cracking furnace as described therein may also significantly reduce the generation of high pressure steam, useful to drive machines, such as compressors and/or pumps of ethylene plants, like cracked gas compressors, propylene refrigeration compressors, ethylene refrigeration compressors, directly or after using the steam for electric power generation. E.g. based on internal research by the present inventor increasing the cracking furnace efficiency from about 40% to about 54% can lead to a steam generation reduction with roughly ⅔. As a result, as a side-effect of the reduced $CO_2$ emission, insufficient steam was available to drive all these compressors.

The present inventor recently invented an improved method and system for driving machines in an ethylene plant addressing a drawback of WO2018/229267, which can reduce the carbon footprint of produced power, i.e. the amount of $CO_2$ emitted per kw of produced power (see non-pre-published European patent application number 19178729.0). Herein an integrated ethylene and power plant system is described, wherein the lower high pressure steam production from the furnaces can be compensated for and that the excess fuel gas produced in the cracking furnace is used to generate significantly more power.

There remains a need for a further way to improve energy-efficiency of ethylene plants and/or to reduce greenhouse gas emissions, which way can be used as an alternative or in addition to known means to accomplish this. It would further be desirable to provide an energy-efficient, low emission ethylene plant which is robust in that it is capable of balancing fluctuations in the electric power capacity of renewable electric power systems.

It has now been found possible to address one or more of these needs by providing an ethylene plant receiving at least a part of its electric power needs from a renewable electric power source, wherein specific fuel fractions are directed inside the ethylene plant in a specific manner.

In particular, the inventor realized that as energy-efficiency increases, more excess fuel leaves the cracking furnace as part of the cracked hydrocarbon gas stream. This fuel typically does not only contain a substantial amount of methane, but also a substantial amount of hydrogen. Hydrogen is a useful product in further chemical processes, notably hydrogenation, but for the methane there is little other use in the current economy than to combust it. This will eventually release $CO_2$ into the atmosphere. The inventor further realized that there would be an advantage in separating the cracked gas not only into one or more fractions enriched in one or more olefins (including an ethylene-enriched fraction), but also at least two different fractions enriched in a gas that serve as fuels within the ethylene plant, namely a hydrogen-enriched fuel fraction and a methane-enriched fuel fraction of the cracked gas.

Accordingly, the present invention relates to an ethylene plant, comprising
- a cracking furnace for converting a hydrocarbon feedstock into a cracked gas stream;
- a separation section configured to provide at least an ethylene-enriched product stream, a hydrogen-enriched fuel stream and a methane-enriched fuel stream from the cracked gas stream;
- a passage way for feeding at least part of the hydrogen-enriched fuel from the separation section to a burner of the cracking furnace and/or a passage way for feeding at least part of the hydrogen-enriched fuel from the separation section to a burner of a waste heat recovery boiler of a combined cycle gas turbine power plant (CCGT);
- a methane storage configured for storing methane-enriched fuel and a passage way for feeding at least part of the methane-enriched fuel from the separation section to the storage;
- the CCGT, comprising a gas turbine—the gas turbine comprising a combustor—and a passage way for feeding at least part of the methane-enriched fuel from the storage to the combustor of the gas turbine of the CCGT, which CCGT is configured to generate electric power and/or to generate high pressure steam to drive a steam turbine forming part of a steam generation circuit of the ethylene plant; and
- an electric power connection configured to provide part of the power for operating the plant, which is a connection to an electric power system to produce electric power from a renewable source.

Usually, the ethylene plant according to the invention comprises
- a cracking furnace for converting a hydrocarbon feedstock into a cracked gas stream, said cracked gas stream comprising ethylene, hydrogen and methane;
- a separation section, configured to separate the cracked gas stream to provide at least an ethylene-enriched product stream, a hydrogen-enriched fuel stream and a methane-enriched fuel stream;
- a passage way for feeding at least part of the hydrogen-enriched fuel from the separation section to a burner of the cracking furnace and/or a passage way for feeding at least part of the hydrogen-enriched fuel from the separation section to a burner of a waste heat recovery boiler of a combined cycle gas turbine power plant (CCGT);
- a methane storage configured for storing liquefied methane-enriched fuel obtained directly from the separation section or after liquefying a gaseous methane-enriched fuel stream from the separation section—and a passage way for feeding at least part of the liquefied methane-enriched fuel from the separation section to the storage;
- a combined cycle gas turbine (CCGT), comprising a gas turbine—the gas turbine comprising a combustor—and a passage way for feeding at least part of the liquefied methane-enriched fuel from the storage to the combustor of the gas turbine of the CCGT via an evaporator unit configured to convert at least part of the liquefied methane-enriched fuel into a gaseous methane-enriched fuel, which CCGT is configured to generate electric power and/or to generate high pressure steam to drive a steam turbine forming part of a steam generation circuit of the ethylene plant; and
- an electric power connection configured to provide part of the power needed to operate the ethylene plant, which power connection is a connection to an electric power system configured to produce electric power from a renewable source.

The invention further relates to a process for producing ethylene from a hydrocarbon feed, comprising the use of an ethylene plant according to the invention.

Generally, the process for producing ethylene from a hydrocarbon feed according to the invention comprises,
- cracking the hydrocarbon in a cracking furnace of an ethylene plant according to any of the preceding claims to produce a cracked hydrocarbon-containing gas, comprising ethylene, hydrogen and methane;
- separating at least part of the cracked hydrocarbon-containing gas at least into an ethylene-enriched product, a hydrogen-enriched fuel and a methane-enriched fuel;
- feeding at least part of the hydrogen-enriched fuel from the separation section to a burner of the cracking furnace and/or feeding at least part of the hydrogen-enriched fuel from the separation section to a burner of a waste heat recovery boiler of a combined cycle gas turbine power plant (CCGT);
- feeding at least part of the methane-enriched fuel, obtained directly from the separation section as a liquid or after liquefying a gaseous methane-enriched fuel stream from the separation section, to a methane storage;
- feeding at least part of the methane-enriched fuel from the storage to the combustor of the CCGT wherein said methane-enriched fuel from the storage is vaporized before it is fed into the combustor; and
- subjecting the vaporized methane-enriched fuel fed to the combustor of the CCGT to combustion in the CGGT, thereby generating electric power and/or thereby generating (high pressure) steam for driving a steam turbine forming part of a steam generation circuit of the ethylene plant, wherein at least a part of the power is electric power produced from a renewable source.

Ethylene plants comprising a cracking furnace provided with one or more burners (configured for combusting a fuel), i.e. a fired cracking furnace, typically in a firebox, benefit in particular highly from the design provided by the present invention. However, in a further advantageous embodiment, another type of furnace configured for thermally cracking a hydrocarbon is present in the ethylene plant. A particularly suitable alternative for a fired cracking furnace is a rotodynamic pyrolysis reactor (a.k.a. RDR). Such cracking furnaces are well known in the art, e.g. from Coolbrook (Helsinki, Finland; Geleen, the Netherlands), see www.coolbrook.com/technology. In yet a further advantageous embodiment, the ethylene plant comprises an electrically heated cracking furnace. In a specific embodiment, the ethylene plant comprises two or more types of cracking furnace.

The description below will focus on a plant with a fired cracking furnace, unless specified otherwise, but the described principles can be applied, mutatis mutandis, to plants comprising another type of cracking furnace, for instance a rotodynamic cracking furnace or an electrically heated cracking furnace. The skilled person will be able to make modifications to the schemes of Figures on the basis of the present disclosure. E.g., as the skilled person will understand, a rotodynamic reactor (RDR) or electrically heated cracking furnace will not require a burner for heating the feedstock. Instead of heating the feedstock mixture from outside the reaction zone with heat from fired (carbon-based) fuel, RDR's high-velocity rotor blades create thermal energy to heat the mixture inside the reaction zone—quickly and much more efficiently. RDR's motors can be driven by electric power. In the absence of a burner in the RDR, an ethylene plant provided with an RDR, will comprise a passage way for feeding at least part of the hydrogen-enriched fuel from the separation section to a burner of a waste heat recovery boiler of the CCGT. Analogously, in the absence of a burner in the electrically heated cracking furnace, an ethylene plant provided with an electrically heated cracking furnace, will comprise a passage way for feeding at least part of the hydrogen-enriched fuel from the separation section to a burner of a waste heat recovery boiler of the CCGT.

The present invention allows the use of a large consumer of fuel (and/or another energy source) and producer of fuel—namely the ethylene plant—to provide a means to temporarily store power in the form of methane-rich fuel to overcome power swings related to renewable power sources. In addition, by replacing methane-rich gas by hydrogen (formed in the ethylene plant during cracking) as a major supply of heat for the cracking furnace, methane-rich fuel is made available instead of hydrogen as an energy supply for generating power that can be used elsewhere. This fuel provides a more suitable fuel gas for running gas turbines than hydrogen and is easier to store. This invention offers a method for the large-scale introduction of renewable power into the grid, largely solving the issues related to large fluctuations of the power from these renewable sources. By using the (probably) largest fuel consumer and producer in the petrochemical industry, the ethylene plant, as a battery, storage of the power during the peak periods can be arranged in the form of storage of liquefied methane-rich gas. During the periods that renewable power availability is low or even absent, the stored methane-rich gas can be used to supply the power using a combined cycle gas turbine (CCGT) system for power generation.

The invention thus further relates to a method for temporarily storing renewable power using an ethylene plant or process according to the invention.

The invention thus further relates to a method for indirectly converting hydrogen to methane-rich gas using an ethylene plant or process according to the invention.

The present invention pushes the boundaries of lowering specific $CO_2$ emissions further, compared to the above cited documents. In particular, the present invention provides a practical way to effectively use electric power from renewable sources into the ethylene plant, also when availability of power from renewable sources is not sufficient at all times, e.g. due to changes in weather (e.g. solar, wind), due to the day-night cycle (solar), due to fluctuations in supply of needed renewable energy source (hydro, biomass), due to peaks in electric power demands exceeding renewable power availability, or due to unforeseen drop in renewable power capacity (e.g. malfunctioning of the renewable power plant or disturbance in electric power supply passage way) as will be further elaborated below.

Thus, the present invention combines electric power from renewable sources with electric power and/or steam generated by the ethylene plant, of which the CCGT is an integral part. The total combined power output can be balanced (e.g. tuned or stabilized) in response to fluctuating output of the renewable electric power or in response to fluctuating demand by tuning the power generated by the CCGT. This requires introduction of a fuel storage to store the excess fuel gas from the ethylene plant, during a period that the renewable power is available in excess. During a period wherein there is a deficit in the renewable power, the power level can be maintained by utilizing the CCGT power plant. In this situation, the CCGT is run on excess fuel gas coming directly from the ethylene plant and/or in addition on stored fuel gas. In this way, electric power can be used within the plant and/or supplied to the grid in a more reliable and continuous way. In accordance with the invention it is feasible to reduce specific $CO_2$ emission per tonne of ethylene produced by at least about 30%, compared to a conventional ethylene plant with a conventional cracking furnace. At least for a fired cracking furnace, this reduction is achieved when the cracking furnace firebox efficiency is increased from 40% to well over 50%. A high efficiency furnace has been specified in the referenced earlier patents as having a firebox efficiency of over 48%. See the Examples below.

This is achieved by preferentially firing excess hydrogen rich fuel gas for heating the cracking furnace along with at least part of the methane rich gas. The excess methane-rich gas, that is produced due to the presence of a high efficiency cracking furnace, can be used for storage during peak loads and can be made available during periods of insufficient availability of renewable power. It can be fed to the combustion chamber of the gas turbine or it can be used for supplemental firing in the waste heat recovery boiler of the CCGT.

The inventor realized there is an advantage in specifically using the methane-enriched stream for this purpose, which may even affect $CO_2$ emissions positively: in particular, hydrogen storage is more complicated than methane storage, requiring higher pressures and/or lower temperatures, potentially costing additional energy for storing equivalent buffers.

In addition, while cracking furnaces are generally designed to handle fuels containing a substantial amount of hydrogen, gas turbines are not. When hydrogen is introduced in the combustion chamber of a gas turbine, the corresponding relatively high flame temperature can cause overheating of the gas turbine. Thus, the choice for using a methane-enriched fuel as a buffer can offer both practical advantages in terms of simplicity of design of the system as well as a reduction of the $CO_2$-footprint.

FIG. 1 schematically shows an ethylene plant/process of the invention, of which the CCGT typically forms an integral part, incorporating power from a renewable power source and providing storage for the resulting excess methane-enriched fuel.

FIG. 2 schematically shows a flow scheme for a plant/process wherein an electrolyzer is provided, indicating flow directions of electric power and methane-enriched fuel.

Figure 11:
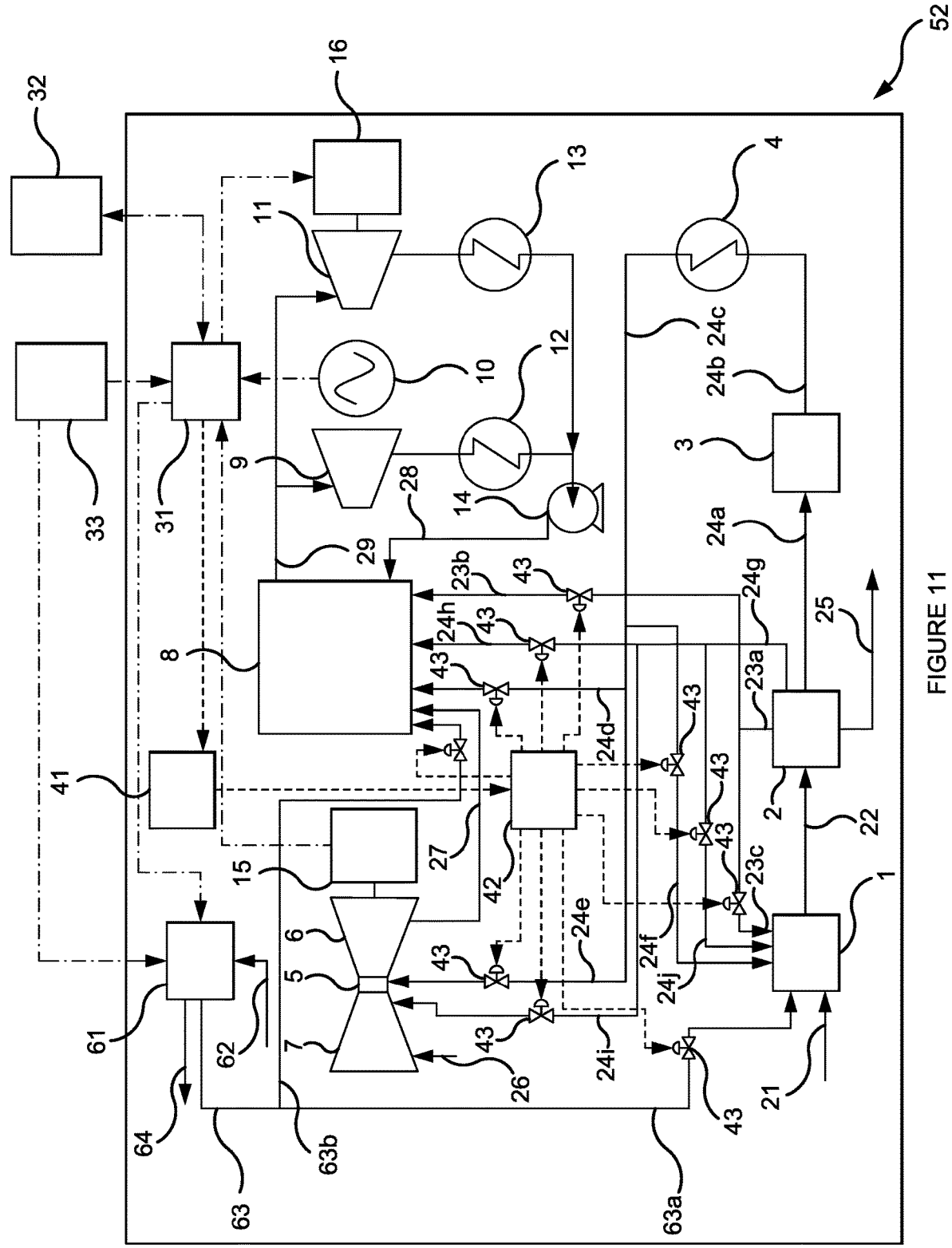

FIG. 11 schematically shows an ethylene plant/process according to the invention, wherein an electrolyzer is provided. It incorporates power from a renewable power source and providing storage for the resulting excess methane-enriched fuel.

In the Figures, the solid lines between the units generally represent a passage way for (or stream of) a fluid (gaseous, liquid); the dotted lines ( . . . ), e.g. between units 31, 41, 42 and 43, represent a communication/regulation signal and the dashed lines (_._.), notably between units 10, 15, 16, 31-33 and 61 represent electric power. Further, boxes formed by bold solid lines (notably boxes 51, 52, 139, 141, 142) are used to show what belongs to the (integrated low emission) ethylene (and power) plant in the illustrative embodiments shown in the figures.

The skilled person will be able to design and operate suitable operational units of the ethylene plant, such as the cracking furnace, the separation section, means for liquefying the methane-enriched fuel (such as an ethylene plant's chilling train), the methane storage, the CCGT, the renewable electric power system, optional equipment, such as an electrolyzer (further discussed below), etc. using the present disclosure in combination with common general knowledge and optionally one or more of the documents cited herein.

Figure 1:
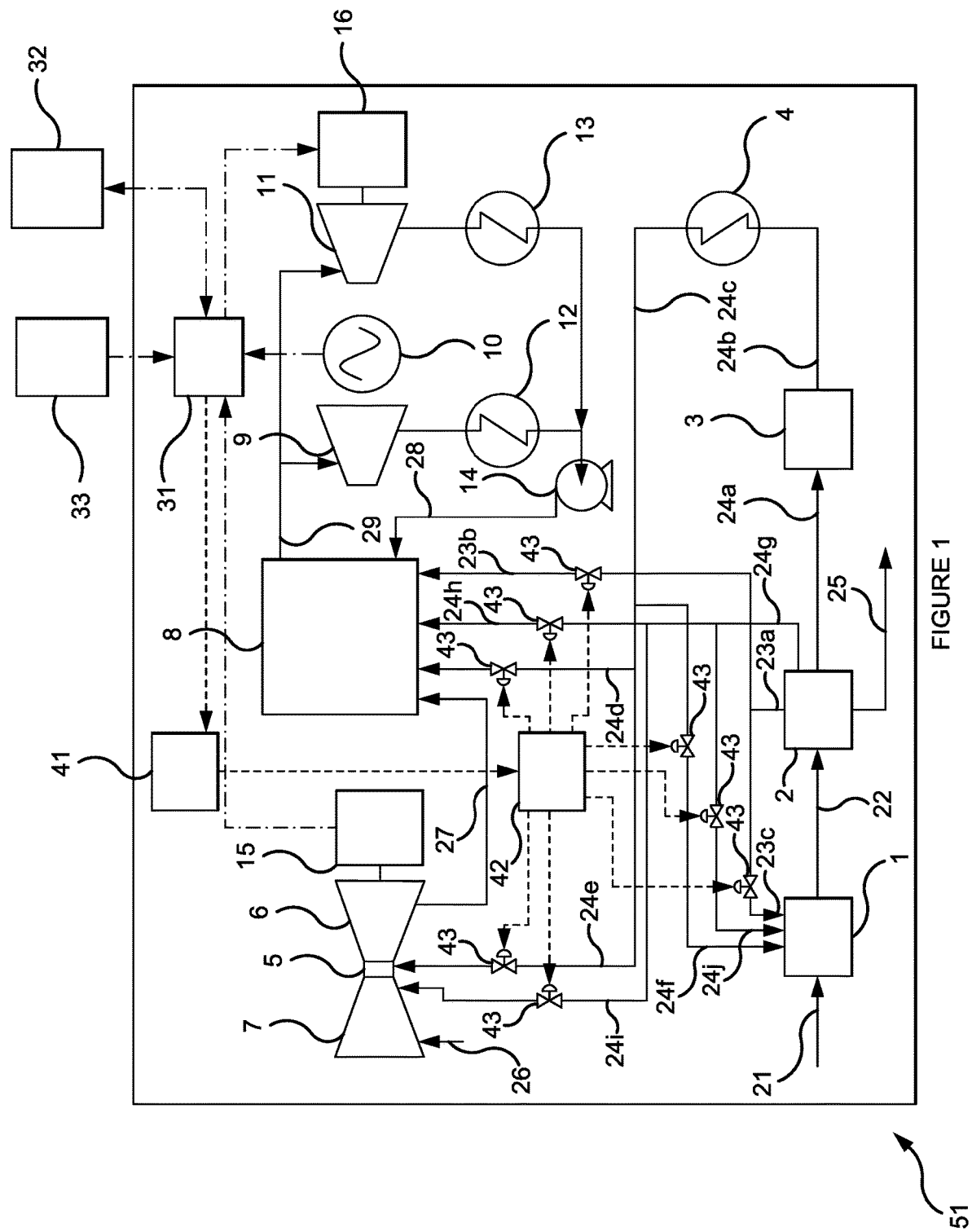
Figure 2:
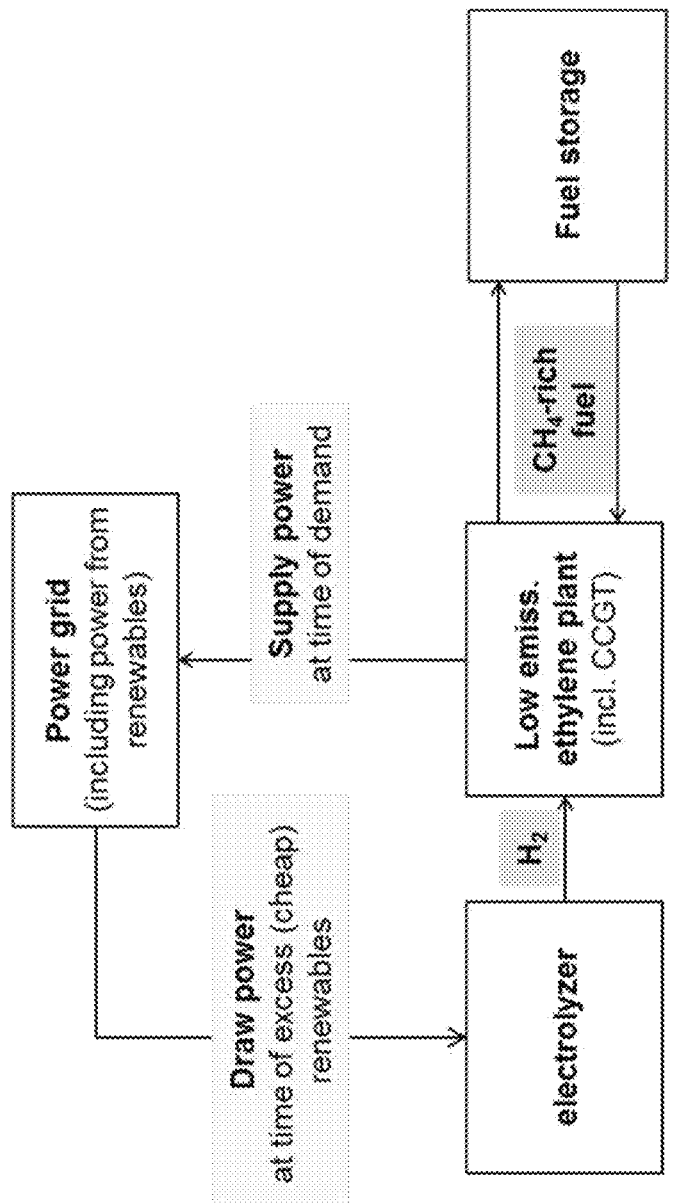

FIG. 1 schematically shows an integrated low emission ethylene and power plant with renewable power import (51) according to the invention. In use, hydrocarbon feedstock

(21) is fed to the cracking furnace (1), which is heated with fuel, typically with methane-rich fuel and/or hydrogen rich fuel. Items 23a-23c are hydrogen-enriched fuel streams; items 24a-24j are methane-enriched fuel streams. The cracked gas (22) is separated into at least an ethylene-enriched product stream (25), a hydrogen-enriched fuel stream (23a) and at least one methane-enriched fuel stream (24a) in the separation section (2). The methane-enriched fuel stream can be obtained as a liquefied stream in the separation section (2) or as a gas of which at least part is subjected to liquefying. It is also possible to obtain both a liquefied methane-enriched stream and a gaseous methane-enriched stream in the separation section (2). Typically, in a plant comprising a fired cracking furnace, the hydrogen-enriched fuel or part thereof is returned to a burner of the cracking furnace (1)—e.g. as shown in FIG. 1 (item 23c)—although alternatively or in addition a passage way for feeding at least part of the hydrogen-enriched fuel from the separation section to a burner of a waste heat recovery boiler (8) of the CCGT may also be provided (item 23b). A methane-enriched fuel passage way from the separation section (2) back to a burner of the cracking furnace (e.g. via fuel lines 24g+24j) and or a methane-enriched fuel passage way from the separation section (2) to the gas turbine combustion chamber (5) may also be provided (e.g. via fuel lines 24g+24i). A passage way (24a) is provided to feed a methane-enriched fuel stream into the methane storage (3), wherein the fuel will typically be stored in a liquefied state, until further use. A passage way (24b) is provided to feed at least part of the liquefied methane-enriched fuel from the storage (3) to an evaporator (4) to provide gaseous methane-enriched fuel from it, which can then be fed to a combustion chamber (5) of a unit of the combined cycle gas turbine circuit. In FIG. 1, a fuel line (24c, 24e) is shown to a combustion chamber (5) of the gas turbine (6) of the CCGT, which also comprises a combustion air compressor (7). This compressor provides required air (26) for the combustion. This combustion air compressor may be integrated with the gas turbine (6), e.g. as shown, but can also be driven by other means, such as a steam turbine or an electric motor. The gas turbine (6) is configured to drive unit 15, which is a power plant electric power generator or ethylene plant compressor. In case the gas turbine drives an electric power generator the power is typically sent to the internal power grid (31), as shown in FIG. 1. The latter power connection is not required when the gas turbine drives an ethylene plant compressor.

A passage way from the evaporator (4) to the cracking furnace (1) may be provided (lines 24c, 24f).

A passage way for fuel to a waste heat recovery boiler (8) may also be provided, e.g. via fuel line 23b and/or via fuel lines 24g+24h from separation section 2; and/or line 24d from the evaporator 4 and line 24c. In use, power can be generated and/or an ethylene plant can be supplied with high pressure steam (29) by the CCGT. A passage way is provided for exhaust gas (27) from the gas turbine (6) to a waste heat recovery boiler (8), which generates (very) high pressure steam used to operate a steam turbine (9) configured to generate electric power, by means of driving an electric power generator (10) and/or to operate a steam turbine (11) configured to operate an ethylene plant compressor and/or pump (16). In case the ethylene plant compressor or pump is not driven by the steam turbine, an electro motor can be used to drive an ethylene plant machine, using an electric power connection connected to the internal grid (31). In this way, power can be provided from a renewable source. Downstream of the steam turbine(s) (9, 11) a surface condenser (12, 13) is provided to condense the steam leaving the steam turbine(s). The condensed water can then be fed back to the waste heat recovery boiler (8) via a pump (14), as boiler feed water (28). The plant further comprises an internal power grid (31), from which the plant units can receive electric power when needed and to which electric power generated in the combined cycle gas turbine circuit can be supplied. The plant is connected to the external power grid (32) via the internal power grid (31). In FIG. 1, the renewable power source (33) is advantageously connected to the plant via the internal grid, but it is also possible to obtain renewable power only via the external grid or via both the external and the internal grid. FIG. 1 further shows a power output control system (41), a firing control system (42) and several control valves (43) for regulating the distribution of fuel streams to the cracking furnace (1), the combustion chamber (5) and the waste heat recovery boiler (8).

FIG. 11 largely resembles FIG. 1. The plant of FIG. 11 further comprises an electrolyzer (61) configured for using electric power to convert water (62) into hydrogen (63) and oxygen (64). The presence of an electrolyzer to convert water to hydrogen for use as fuel in the cracking furnaces, in order to produce more excess fuel, thus providing a method for the temporary storage of renewable power in conjunction with an ethylene plant according to the invention, as defined in claims 7-17 and 22-24, and further described in the description can be considered as an invention on its own. The hydrogen produced in the electrolyzer is for use as fuel in a plant according to the invention. Thus, FIG. 11 shows an integrated low emission ethylene and power plant (52) with renewable power import and electrolyzer. At least part of the electric power used by the electrolyzer is renewable power (from renewable power source 33). It is also possible to use power from the internal grid (31), e.g. from generator 10, to electrolyze water in the electrolyzer. A passage way may be provided to feed the generated hydrogen from the electrolyzer to a burner of the cracking furnace (63a) and/or a passage way may be provided for feeding generated hydrogen from the electrolyzer to a burner of the waste heat recovery boiler of the CCGT (63b). See the description of FIG. 1 for a discussion of the other items.

The cracking furnace can in principle be based on known conventional cracking furnaces, e.g. on U.S. Pat. No. 4,479, 869.

For a particularly advantageous use of the invention as a temporary storage of power and/or a particularly advantageous reduction in $CO_2$ emissions, the cracking furnace preferably is a high efficiency furnace. A higher cracking furnace efficiency can make a lot of methane-rich fuel gas available for temporary storage and can minimize the firing of relatively expensive hydrogen.

In particular, the high efficiency cracking furnace can be based on WO 2018/229267 or on non-pre-published EP application number 19198787.4, of which the contents are incorporated by reference, in particular the claims, Figures and descriptions of the Figures. These two documents describe—amongst others—advantageous arrangements for providing a high efficiency (in terms of required unit of energy per unit of cracked product) with respect to a feed/effluent transfer line exchanger (TLE) and a boiler coil or a high temperature coil in series with the feed/effluent TLE.

Preferably, the (high efficiency) cracking furnace of an ethylene plant of the invention is configured to carry out a method for cracking hydrocarbon feedstock, comprising a first feedstock preheating step and a second feedstock preheating step, wherein the first feedstock preheating step comprises preheating hydrocarbon feedstock by hot flue gasses of a cracking furnace system,
wherein the second feedstock preheating step comprises further preheating of the feedstock by waste heat of cracked gas of the cracking furnace system before entry of the feedstock into a radiant section of the cracking furnace system. Such method is disclosed, e.g., in WO 2018/229267, but a cracking furnace system as described in non-pre-published EP application number 19198787.4 can also advantageously be configured to carry out such method. Said method comprising the first feedstock preheating step and the second feedstock preheating step further preferably comprises one or more of the following:

said second feedstock preheating step is performed using a transfer line exchanger;
the boiler water is fed from a steam drum of the cracking furnace system to a boiler coil in the convection section of the cracking furnace system, wherein said boiler water is heated, preferably evaporated, by hot flue gasses, and wherein a mixture of water and vapor is returned to said steam drum;
the hydrocarbon feedstock is mixed with a diluent, such as dilution steam, to provide a feedstock-diluent mixture before the second feedstock preheating step;
high pressure steam is generated by waste heat of cracked gas of the cracking furnace system, using a secondary transfer line exchanger located downstream of the transfer line exchanger;
boiler feed water is preheated by hot flue gasses before entry into a steam drum of the cracking furnace system;
an adiabatic flame temperature in the radiant section is increased by introduction of an oxidant, preferably pure oxygen, directly into the radiant section of the cracking furnace system;
an adiabatic flame temperature in the radiant section is increased by the introduction of combustion air as a main oxidant and oxygen as a secondary oxidant, preferably highly nitrogen depleted oxygen, directly into the radiant section of the cracking furnace system in absence of a flue gas recirculating circuit;
the oxidant, such as combustion air and/or oxygen, is preheated before introduction into the radiant section;
the oxidant is preheated by flue gasses of the cracking furnace system;
an adiabatic flame temperature in the radiant section of the cracking furnace system is controlled by recirculating at least part of the flue gas;
oxygen is mixed with the recirculated flue gas prior to entry into the furnace firebox;
boiler feed water is preheated before entry into a steam drum of the cracking furnace by a heat pump circuit;
organic liquid is heated by hot flue gasses from the cracking furnace system and returned to a vapor-liquid separating device of the heat pump circuit;
heat from high pressure vapor is transferred to the boiler feed water by a condenser of the heat pump circuit;
heat from a condensed liquid generated in a heat sink of the heat pump circuit is transferred by a feed effluent exchanger to saturated vapor generated in a heat source of the heat pump system.

In an advantageous embodiment, the cracking furnace comprises a convection section, a radiant section and a cooling section,
wherein the convection section includes a plurality of convection banks configured to receive and preheat hydrocarbon feedstock,
wherein the radiant section includes a firebox comprising at least one radiant coil configured to heat up the feedstock to a temperature allowing a pyrolysis reaction,
wherein the cooling section includes at least one transfer line exchanger,
wherein the cracking furnace is configured to preheat the feedstock by the transfer line exchanger before entry into the radiant section.

Such cracking furnace, preferably also comprises one or more of the following:

the convection section comprises a boiler coil configured to generate saturated steam, wherein said boiler coil is preferably located in a bottom part of the convection section;
the cracking furnace system further comprising a steam drum which is connected to the boiler coil and/or to the secondary transfer line exchanger (TLE), which boiler coil and/or secondary TLE are configured to generate saturated steam;
the convection section is also configured for mixing said hydrocarbon feedstock with a diluent, preferably dilution steam, providing a feedstock-diluent mixture, wherein the transfer line exchanger is configured to preheat the feedstock-diluent mixture before entry into the radiant section;
the cracking furnace system further comprises a secondary transfer line exchanger, wherein the secondary transfer line exchanger is configured to generate saturated high pressure steam;
the firebox is configured such that a firebox efficiency is higher than 40%, preferably higher than 45%, more preferably higher than 48%;
the convection section comprises an economizer configured to preheat boiler feed water for the generation of saturated steam;
the convection section comprises an oxidant preheater, preferably located downstream in the convection section, configured to preheat oxidant, for example combustion air and/or oxygen, before introduction of said combustion air into the firebox;
the cracking furnace system is configured for oxygen introduction into the radiant section, preferably in the absence of external flue gas recirculation;
the cracking furnace system further comprises an external flue gas recirculation circuit configured to recover at least part of the flue gas and to recirculate said flue gas to the radiant section to control flame temperature, preferably the external flue gas recirculation circuit comprising a flue gas ejector configured to introduce oxygen into the recirculated flue gas prior to entry into the firebox;
the cracking furnace system further comprises a heat pump circuit including an evaporator coil located in the convection section and a condenser, wherein the heat pump circuit is configured such that the evaporator coil recovers heat from the convection section and the condenser transfers said heat to boiler feed water, which is typically configured for preheating boiler feed water;

See also WO 2018/229267 for further details.
In particular, the usefulness of said heat pump circuit for preheating boiler feed water is not restricted to the cracking furnace system of WO 2018/229267.
Thus, in an advantageous embodiment, the ethylene plant of the invention comprises a cracking furnace system provided with a heat pump circuit for preheating boiler feed water of the cracking furnace system including an evaporator coil arranged to recover heat from flue gas in a convection section of the cracking furnace system, and a condenser configured to transfer said heat to boiler feed water.

Said heat pump circuit preferably comprises one or more of the following:
- it comprises a vapor-liquid separating device connected to the evaporator coil and arranged to separate vapor from a liquid-vapor mixture coming from said evaporator coil;
- it comprises a feed effluent exchanger arranged to superheat vapor generated in a heat source, and to subcool liquid generated in a heat sink, of the heat pump circuit;
- it comprises a compressor arranged to raise a vapor pressure such that a condensing temperature of said vapor exceeds a desired temperature to be transferred to the boiler feed water.

See also WO 2018/229267 for further details.

In a further advantageous embodiment, a cracking furnace system is provided comprising a convection section, a radiant section and a cooling section, wherein the convection section includes a plurality of convection banks, including a first high temperature coil, configured to receive and preheat hydrocarbon feedstock, wherein the radiant section includes a firebox comprising at least one radiant coil configured to heat up the feedstock to a temperature allowing a pyrolysis reaction,
wherein the cooling section includes at least one transfer line exchanger,
wherein the system is configured such that the feedstock is preheated by the transfer line exchanger before entry into the radiant section.

This cracking furnace system preferably comprises one or more of the following:
- the convection section includes a second high temperature coil configured to preheat feedstock after exit of the feedstock from the transfer line exchanger and before entry into the radiant section;
- the second high temperature coil is preferably located in a bottom part of the convection section;
- the convection section is also configured for mixing said hydrocarbon feedstock with a diluent, preferably dilution steam, providing a feedstock-diluent mixture, wherein the transfer line exchanger is configured to preheat the feedstock-diluent mixture before entry into the radiant section, and wherein the second high temperature coil is configured to preheat the feedstock-diluent mixture after exit of the feedstock-diluent mixture from the transfer line exchanger and before entry into the radiant section;
- a steam drum configured to generate saturated high pressure steam, wherein—more preferably—the convection section includes at least one high pressure steam superheater configured to superheat high pressure steam coming from the steam drum;
- a secondary transfer line exchanger which is located downstream from the primary transfer line exchanger and which is connected to the steam drum, and which is configured to at least partly vaporize boiler water coming from the steam drum.

Such design has advantages comparable to the design based on WO2018/229267, as described above, in particular with respect to reduced fuel consumption, improved firebox efficiency and reduced $CO_2$ emission. See also EP application number 19198787.4 for further details.

Said cracking furnace system is advantageously used in a method according to the invention, wherein the method comprises a first feedstock preheating step, a second feedstock preheating step, and a third preheating step before entry of the feedstock into a radiant section of the cracking furnace system,
wherein the first feedstock preheating step includes preheating hydrocarbon feedstock by hot flue gasses of a cracking furnace system using a first high temperature coil, wherein the second feedstock preheating step includes further preheating of the feedstock by waste heat of cracked gas of the cracking furnace system using a transfer line exchanger, wherein the third feedstock preheating step includes further preheating of the feedstock by hot flue gasses of the cracking furnace system using a second high temperature coil. In a preferred embodiment, the hydrocarbon feedstock is mixed with a diluent, such as dilution steam, to provide a feedstock-diluent mixture before the second feedstock preheating step. In a preferred embodiment high pressure steam is generated by waste heat of cracked gas of the cracking furnace system, using a secondary transfer line exchanger located downstream of the transfer line exchanger. See also EP application number 19198787.4 for further details.

Separation sections for separating cracked gas in different fraction are generally known in the art. E.g. one can use conventional distillation, such as cryogenic distillation, to obtain an ethylene-enriched product stream (compared to the cracked gas), a hydrogen-enriched fuel stream (compared to the cracked gas) and a methane-enriched fuel stream (compared to the cracked gas). Further streams may be obtained as well, such as a propylene-enriched stream (compared to the cracked gas) and/or a butadiene-enriched stream (compared to the cracked gas). The methane-enriched fuel stream may be obtained in the separation section as a liquefied fuel or the liquefied methane-enriched fuel stream may be obtained by liquefying a gaseous methane-enriched fuel downstream of the separation section, preferably making use of a chilling unit of the ethylene plant. Advantageously, both a gaseous a methane-enriched fuel stream and a liquefied methane-enriched fuel stream are obtained in the separation section. In a preferred embodiment, a chilling section of the ethylene plant is configured to progressively condense the lighter fractions of the cracked gas. For this, propylene, ethylene and/or methane-rich refrigeration streams may be used. The hydrogen-enriched fuel stream is obtained from this progressive condensation as a gas (vapor), while a methane-enriched stream is obtained as a liquid fraction. The methane-enriched liquid fraction is then usually separated in a demethanizer to yield an ethylene-rich fraction as bottom product and a methane-rich fraction as top product (methane-enriched fuel).

When desired, the separation section can comprise one or more units to further treat, e.g. to increase the concentration of a certain component or to remove undesired components before further use. If hydrogen or methane is to be used for a different purpose than for energy production in the plant, this hydrogen or methane can be obtained from a hydrogen-enriched stream or a methane-enriched stream after further separation/purification. Thus, e.g. hydrogen can be obtained for use in a hydrogenation process.

The hydrogen-enriched fuel from the separation section or a part thereof is typically fed to the cracking furnace (in case of a fired cracking furnace), preferably along with part of the methane-enriched fuel gas, to balance the fired heat requirements of the cracking furnace. Alternatively, or in addition, hydrogen-enriched fuel can be fed to the waste heat recovery boiler of the CCGT. When there is an excess of fuel, storage of excess methane-enriched fuel is advantageous over storage of hydrogen-enriched fuel. The excess methane-enriched fuel to be stored is typically fed to the methane storage in liquefied form, and—when taken from the storage, fed to a burner in gaseous form after evaporating it with an evaporator. The evaporation is preferably integrated with the chilling section of the ethylene plant to recover the cold as much as possible.

It is well known to store liquefied methane (namely liquefied natural gas, LNG) at about atmospheric pressure at roughly −160° C. For the present invention this is also possible, although storage at super atmospheric pressure is also an option. At least in some embodiments of the present invention it is advantageous to store the methane-enriched fuel at elevated pressure, e.g. at about a burner supply pressure, of about 4 barg or more, or about 10 barg or more. In practice, the pressure is usually about 20 barg or less, in particular 15 barg or less. Storing at elevated pressure, facilitates handling of daily fluctuations in the volumes produced and needed. It also allows to feed the fuel to the burner without the aid of pressurizing means, such as a cryogenic pump, to bring the fuel to the required burner supply pressure. In an embodiment, wherein it is beneficial for the cold integration, storing it at even higher pressure than available at its source in the ethylene plant can be advantageous. In this case, the fuel is preferably compressed and subsequently cooled against a suitable heat sink to produce a liquefied gas suitable for storage, which may be liquefied as a true liquid or as a supercritical fluid.

Storing an amount of hydrogen representing a specific calorific value, is more complicated than storing an amount of methane representing the same calorific value. The hydrogen storage requires higher compression levels and/or lower storage temperatures, which costs additional energy. Furthermore, methane-enriched fuel is preferred over hydrogen for use as a fuel of other units than the cracking furnace, such as a gas turbine of a CCGT, due to the higher adiabatic flame temperature when hydrogen is combusted, which is less well tolerated by such units.

The methane-enriched fuel obtained from the cracked hydrocarbon gas that is stored, is generally stored in the methane storage in a liquefied form. The methane storage usually is equipped with a boil-off compressor and a heat exchanger at the discharge of the compressor configured to reject the heat to a suitable heat sink. E.g. a condenser may be provided, configured to recondense any vapor from the storage. In case the compressor outlet operates above the critical point this will be a cooler to reject the required heat.

Part of the methane-enriched fuel obtained from the cracked gas may be returned to a burner of the cracking furnace (in case of a fired cracking furnace). The fraction to be returned can be selected from any of the methane-enriched fractions obtained in a process according to the invention. In a preferred embodiment, a gaseous methane-enriched fuel fraction is used for this purpose, more preferably without having been stored. In particular, one may use methane-enriched fuel obtained as a gas fraction from the chilling and demethanization section, such as present in the chilling section of the separation section. The chilling section may be a progressive condensation system, cooling down the cracked gas and flashing it in a number of flash vessels in series to obtain a hydrogen-enriched (gas) stream and a number of methane-enriched liquid streams from these flashes. These methane-enriched streams may be sent to a demethanization section to produce at least a methane-enriched top and/or side product, in gaseous phase and/or in liquid phase, and at least a bottom product lean in methane, preferably rich in ethylene product. In this case, the gaseous methane-enriched product can be used directly. Alternatively, a liquid methane-enriched stream may be used, but it would have to be evaporated to be used directly (without storage).

At least part of the methane-enriched fuel is used for another purpose than being combusted in the cracking furnace. At least a part of the methane-enriched fuel that has been stored in the methane storage is typically combusted in the combined cycle gas turbine to generate electricity and/or high pressure steam, which can be used to drive steam turbines in the ethylene plant. In an embodiment, part of the gaseous methane-enriched fuel from the separation section is fed to a burner of the waste heat recovery boiler of the CCGT.

Usually, the CCGT is operated with a turn-up/turn-down ratio operating range of 20-140%, preferably of 30-130% operating range, more preferably of 40-120%.

The percentage of methane-enriched fuel stream that is stored before further use, the percentage of methane-enriched fuel stream that is returned to the cracking furnace (directly or after storage) and the percentage of methane-enriched fuel that is combusted (directly or after storage) in the CCGT may vary widely over time, dependent on the available power from the renewable source, the required production of ethylene (and optionally other olefins) and variations in process conditions.

In practice, the liquefied methane-enriched fuel from the methane storage is usually is fully evaporated before being sent to the burner(s) (of a fired cracking furnace or of a CCGT). This can be done using, e.g., at least an LMG (Liquefied Methane-enriched Gas) evaporator. In addition, it is also preferred to have the fuel gas temperature to be raised to a temperature level close to ambient conditions and to recover (as much as possible of) the cold associated with the evaporation and superheating of the LMG. This can best be done by integration of the LMG evaporation and superheating with the chilling train, such as to reduce the load on the refrigeration system(s). When expanding the liquefied methane-enriched fuel, it will conveniently be flashed to very low temperature, which can be used in the chilling train to help to reach very low temperature levels. This can be used to minimize losses of ethylene to the fuel gas and recover as much of the cold as possible. So this stream would preferably be sent to the cold end of the chilling train. When storing at relatively low super-atmospheric pressure, such as of about 4 to about 5 barg, flashing will be marginal. Yet, then it will still be preferred to bring the liquid to the cold end of the chilling train for the same reasons: to lower loss of ethylene product and increase recovery of cold.

The gas turbine combined cycle power plant unit generally operates as follows: the fuel gas (methane-enriched fuel) is combusted in the combustion chamber of a gas turbine by combustion air supplied to the combustion chamber by a combustion air compressor. The produced flue gas is typically let down over a gas turbine to generate electric power via a generator. The combustion air compressor, the combustion chamber and the gas turbine are typically integrated in the same machine. The gas turbine drives both the combustion air compressor as well as the generator. The flue gas from the gas turbine is sent to a waste heat recovery boiler with auxiliary firing to generate very high pressure steam from boiler feed water. The very high pressure steam is advantageously used to drive a generator by letting it down in a condensing steam turbine with a surface condenser. In the surface condenser the steam is fully condensed. Except for a small blow down, practically all the condensed steam is collected and pumped back to the waste heat recovery boiler as boiler feed water to close the loop.

In practice, the condensate is usually first fed to a deaerator to mix it with demineralized make-up water and strip it with steam to remove air (not shown in FIG. 1). Instead of driving a generator, the gas turbine can also be used to drive one or more of the ethylene plant compressors (see also EP application 19178729.0). In addition, very high pressure steam can be exported from the waste heat recovery boiler to one or more of the steam turbines in the ethylene plant instead of being used to generate power via a steam turbine in the power plant (see also EP application 19178729.0).

The electric power connection is a connection to an electric power system configured to produce electric power from a renewable source. It can be a connection to the ethylene plant's internal power grid to supply at least part of the required power to drive machines, a power plant unit that forms part of the ethylene plant, a larger industrial complex of which the ethylene plant forms a part, or to an external (remote) power plant which is connected to the same electric grid as the ethylene plant according to the invention. Preferably, the electric power system configured to produce electric power from a renewable source is an integrated part of the ethylene plant or an integrated part of an industrial complex of which the ethylene plant is a part and/or the electric power system is connected to the ethylene plant via an external electricity grid.

The electric connection of the ethylene plant preferably not only allows receiving electric power from the power plant providing renewable electric power, but is preferably also configured to allow the supply of surplus power outside the ethylene plant, e.g. to another facility outside the ethylene plant within the same industrial complex or to the electric grid. Thus, in a preferred embodiment, both the renewable power and the CCGT produced power are connected to an internal plant grid, and further a connection is present to the external grid. This external connection provides a well-balanced power stream to the grid.

The electrical power system providing electricity from a renewable source comprises usually one or more power systems selected from the group consisting of wind power systems, solar energy systems, hydropower systems, geothermal energy systems and osmotic power systems (also known as blue energy). Alternatively, or in addition use can be made of one or more systems configured to generate electricity from biomass and/or one or more systems configured to generate electricity from a bio-renewable fuel, e.g. bio-ethanol or biodiesel.

In an advantageous embodiment, the ethylene plant has an ethylene plant steam generation circuit and a power plant circuit as described in non-pre-published EP application number 19178729.0.

Thus, in an advantageous embodiment, an ethylene plant steam generation circuit is present, comprising:
the cracking furnace for converting a hydrocarbon feedstock into cracked gas, wherein the cracking furnace is configured to generate high pressure steam, in particular very high pressure steam from boiler feed water;
a steam turbine configured to be driven by said (very) high pressure steam;
a process compressor configured to be driven by the steam turbine;
a condenser configured to condense at least part of the (very) high pressure steam;
a pump configured to pump the condensed steam to the cracking furnace as boiler feed water;
the power plant circuit comprising a waste heat recovery boiler configured to recover heat as (very) high pressure steam, wherein the system further comprises a first connection between the ethylene plant steam generation circuit and the power plant circuit configured to lead at least part of the high pressure steam from the waste heat recovery boiler to the at least one steam turbine of the ethylene plant steam generation circuit to drive said at least one steam turbine.

Such system is particularly suitable for driving machines, for example process compressors, in an ethylene plant steam generation circuit. When driving machines, this in particular includes the steps of:
recovering heat as high pressure steam from a cracking furnace;
providing said high pressure steam to at least one steam turbine, wherein the steam turbine is configured to drive a machine, such as a process compressor;
condensing at least part of the high pressure steam in a condenser;
pumping condensed steam as boiler feed water back to the cracking furnace;
wherein the method also includes the step of:
recovering heat as high pressure steam from a waste heat recovery boiler of a power plant circuit;
providing at least part of the high pressure steam from the power plant circuit to the at least one steam turbine of the ethylene plant steam generation circuit.

Such system is for instance particularly suitable for use in a process according to the invention, wherein excess fuel from the cracking furnace of the ethylene plant steam generation circuit is provided to the waste heat recovery boiler of the power plant circuit for auxiliary firing. In addition, or alternatively, in such process advantageously the waste heat recovery boiler is provided with exhaust gas from at least one gas turbine of the power plant circuit; in particular, excess fuel from the cracking furnace of the ethylene plant steam generation circuit can then be provided to the gas turbine of the power plant circuit for combustion. Said gas turbine can then advantageously be configured to drive a machine, such as a process compressor, of the ethylene plant steam generation circuit. Such embodiment preferably includes the steps of:
providing at least part of the high pressure steam from the waste heat recovery boiler of the power plant circuit to at least one steam turbine of the power plant circuit, wherein the steam turbine is configured to drive a generator for generating power;
condensing at least part of the high pressure steam in a condenser of the power plant circuit;
pumping said condensed steam as boiler feed water back to the waste heat recovery boiler.

In an advantageous embodiment, wherein an ethylene plant steam generation circuit is present (as based on EP application number 19178729.0), and which may be used to drive a machine, the ethylene plant preferably further comprises a second connection between the ethylene plant steam generation circuit and the power plant circuit configured to lead excess hydrogen-enriched gas stream, excess methane-enriched gas stream or both from the separation section to a burner of the waste heat recovery boiler.

The power plant circuit of the ethylene plant having an ethylene plant steam generation circuit and a power plant circuit may further include at least one gas turbine, wherein the at least one gas turbine is connected to the waste heat recovery boiler such that exhaust gas from the at least one gas turbine is recovered by the waste heat recovery boiler. In such embodiment, preferably a further connection is present between the ethylene plant steam generation circuit and the power plant circuit configured to lead at least part of excess hydrogen-enriched gas stream, excess methane-enriched gas stream or both from the ethylene plant steam generation circuit to the at least one gas turbine for combustion.

The ethylene plant steam generation circuit further preferably includes a process compressor which is configured to be driven directly by the gas turbine of the power plant circuit.

The power plant circuit of the ethylene plant preferably includes at least one steam turbine and at least one generator, wherein the circuit is configured to provide at least part of the high pressure steam from the waste heat recovery boiler to the at least one steam turbine of the power plant circuit, wherein the at least one steam turbine is configured to drive the at least one generator for generating power.

The power plant circuit further includes a condenser configured to condense at least part of the high pressure steam, and a pump configured to pump said condensed steam as boiler feed water back to the waste heat recovery boiler.

In a particular advantageous embodiment, the ethylene plant is an integrated ethylene and power plant system, wherein the cracking furnace is a high efficiency cracking furnace including a radiant section, a convection section and a cooling section, wherein the cooling section includes at least one transfer line exchanger configured to preheat feedstock before entry into the radiant section, and wherein a convection section comprises a boiler coil configured to generate saturated steam from flue gas, said boiler coil being preferably located in a bottom part of the convection section.

In a particular advantageous embodiment, the ethylene plant is an integrated ethylene and power plant system, wherein the cracking furnace is a high efficiency cracking furnace including a radiant, wherein the cracking furnace is a high efficiency cracking furnace including a radiant section, a convection section and a cooling section, wherein the cooling section includes at least one transfer line exchanger configured to preheat feedstock before entry into the radiant section, and wherein a convection section comprises a second high temperature coil configured to preheat feedstock after exit of the feedstock from the transfer line exchanger and before entry into the radiant section, said second high temperature coil being preferably located in a bottom part of the convection section.

In an embodiment, the ethylene plant comprises a machine, such as a compressor and/or a pump, configured to be driven by electric power from the CCGT and by electric power from the electric power system configured to produce electric power from a renewable source.

Advantageously, the ethylene plant comprises an automated controller unit, configured to regulate process parameters, in particular selected from the group consisting of fuel flow rates and fuel pressures, to compensate for fluctuations in the electric power provided via the renewable electric power connection. The controller unit is typically an instrument configured to automatically compare set-points with operating points and minimizing the difference, e.g. using PID algorithms. Accordingly, a PID-controller is particularly suitable. Typically, compensation in electric power fluctuations is accomplished by regulating a fuel flow rate and/or pressure in one or more of the passage ways of the ethylene plant for hydrogen-enriched and/or methane-enriched fuels, in response to the (existing or expected) fluctuations, thereby increasing electric power output of the CCGT when electric power provided by said electric power connection decreases (or is expected to decrease) and decreasing electric power output of the CCGT when electric power provided by said electric power connection increases (or is expected to increase).

In an advantageous embodiment, the ethylene plant according to the invention, comprises an electrolyzer, wherein the electric power connection providing electric power from a renewable source is connected to the electrolyzer (schematically shown in FIGS. 2 and 8-11). This electrolyzer is configured to use at least part of the electric power from the renewable source and optionally to use at least part of the electric power generated by the CCGT to generate hydrogen by electrolysis, typically by water electrolysis. Further a passage way is provided in this embodiment for feeding generated hydrogen from the electrolyzer to a burner of the cracking furnace, a passage way to a burner of the waste heat recovery boiler of the CCGT, or both.

Oxygen, also produced by the electrolysis of water, can either be sold or be used for burning fuel, in particular a methane-rich fuel, e.g. in a waste heat recovery boiler of the ethylene plant to burn the methane with a higher oxygen concentration and thus to get a richer $CO_2$ mixture for future carbon capturing. By using renewable electric power to generate hydrogen fuel that is combusted in the cracking furnace, it is possible to further reduce the specific $CO_2$; it allows exporting more excess methane-enriched fuel gas to the CCGT to generate electric power and/or (very) high pressure steam there, instead of firing it in the cracking furnace. By introducing hydrogen into the cracking furnace, the specific emission of the furnace can be reduced and at the same time more excess methane-rich fuel from the ethylene plant can be fired in the CCGT power plant at a higher heat-to-power ratio than in the cracking furnace power generation circuit. Considering that an ethylene plant can have plurality of cracking furnaces, this is a very practical solution for the reduction of the CO2 emissions, contrary to applying carbon capturing on many individual emission sources to reduce these emissions.

Further, any methane-rich fuel not directly combusted in the CCGT can be stored for later use. It is even possible to use this embodiment in times of overproduction of renewable power (e.g. during sunny days for solar energy and during periods of strong wind for wind energy), as the production of hydrogen can then be increased, allowing a further reduction in methane needed for combustion in the cracking furnace and/or the waste heat recovery boiler of the CCGT power plant.

The methane-rich fuel is considerably easier to store than the hydrogen produced by the electrolyzer (which can be used directly without storage). The $CO_2$ emissions associated with compressing hydrogen at high pressure for storage for use in cars can be avoided in this case. The compression/storage of hydrogen instead of methane-enriched fuel would reduce the efficiency with as much as about 25%. In an embodiment, this system allows the specific emissions per tonne of ethylene produced to be reduced in excess of 55% with an availability of the renewable energy of 33% of its maximum capacity per day. With the fuel storage balancing the fluctuating renewable power production, reliable and stable power can be supplied to the grid. As a rule of thumb, with the addition of the electrolyzer, three times more renewable power can be generated than in the scheme of FIG. 1. The electrolyzer is connected to the renewable power source and there is a passage way provided for feeding the hydrogen generated in the electrolyzer to a burner in the ethylene plant, usually a burner of a cracking furnace. FIG. 1 is largely based on European Patent Application 19178729.0, but with the addition of the methane storage and use of hydrogen-enriched fuel and methane-enriched fuel from the cracked gas as described above. Furthermore, in an embodiment making use of the electrolyzer, it is easier to operate the CCGT close to its optimal production point, such that the heat-to-power conversion efficiency is the highest and $CO_2$ emissions are the lowest, by tuning the flow of fuel to it from the fuel storage. For example, if the production of power from the renewable sources is high, the corresponding production of hydrogen is also high, enabling the production of large quantities of methane rich fuel from the ethylene plant. Over-production of methane fuel, resulting in the CCGT operating above the optimum production point, can be subsequently stored for periods of under-production to prevent as much as possible operation of the CCGT below the optimum production point. It should be noted here that the CCGT will operate at its optimum efficiency point if this also meets the power demand from the user side. If provision of renewables is low (i.e. low $H_2$) less methane rich fuel is generated. Additional methane rich fuel required to operate the CCGT at optimum point can be added from the storage. (see FIG. 2).

As used herein, the singular forms "a", "an" and "the" are intended to include the plural forms as well—, e.g. "a cracking furnace" includes "cracking furnaces"; "a burner" includes "a plurality of burners", etc, unless the context clearly indicates otherwise. The term "or" includes any and all combinations of one or more of the associated listed items, unless the context clearly indicates otherwise (e.g. if an "either . . . or" construction is used). It will be understood that the terms "comprises" and "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise, it will be understood that when a connection between structures or components is described, this connection may be established directly or through intermediate structures or components unless specified otherwise.

In the context of this application, the term "about" includes in particular a deviation of 10% or less from the given value, more in particular 5%, more in particular 3% or less.

The term "high pressure steam" (HP steam) is well known in the art. As a rule of thumb, the pressure of HP steam is usually at least about 40 barg. For HP steam that has a pressure 80 barg or more, in particular of about 100 barg to about 130 barg, the term Very High Pressure steam (VHP steam) is used herein. When referred to 'enriched' this means enriched compared to the cracked gas exiting the cracking furnace. The hydrogen-enriched fuel stream will generally have a hydrogen content of more than 50 mole %, typically of about 80-100 mole %. A methane-enriched stream obtained from the cracked gas stream will generally have a methane content of more than 50 mol %, typically of 60-100 mole %. As described above, in a first separation step the cracked gas stream can be separated in a hydrogen-enriched (gas) stream and methane-enriched (liquid) stream (in the chilling and demethanization section), which methane-enriched liquid fraction is thereafter subjected to a further fractionation (in a demethanization section), from which an ethylene-rich fraction and a methane-enriched fuel are recovered; the methane-enriched liquid fraction from the chilling section prior to demethanization will typically have a lower methane content, e.g. of 60-70 mole %, than the methane-enriched fuel to be stored/fed to a burner, which fuel usually has a methane content of 80 mole % or more, typically between about 90 mole % and about 100 mole %.

The invention is described more fully herein with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

For the purpose of clarity and a concise description, features are described herein as part of the same or separate embodiments, however, it will be appreciated that the scope of the invention may include embodiments having combinations of all or some of the features described.

Next, the invention is illustrated by the following Examples.

EXAMPLES

Example 1 (Reference)

An ethylene plant arrangement having a low emission cracking furnace as per WO2018/229267, adapted as per EP application number 19178729.0 to include an integrated power plant, is provided and compared to an ethylene plant arrangement with a conventional cracking furnace (i.e. not low emission).

Figure 3:
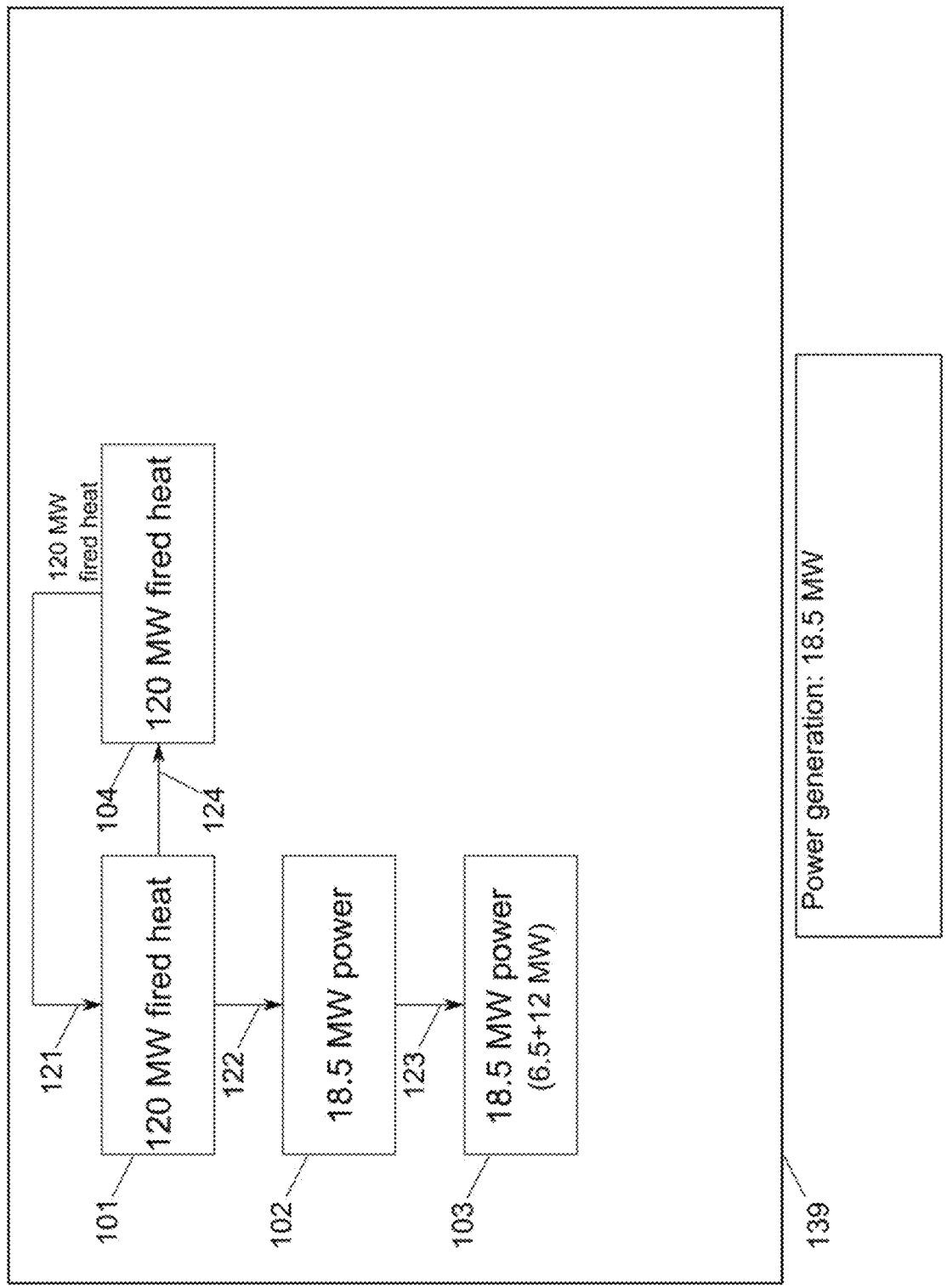
FIG. 3 shows results for an ethylene plant arrangement with a conventional cracking furnace (i.e. not low emission)
Figure 4:
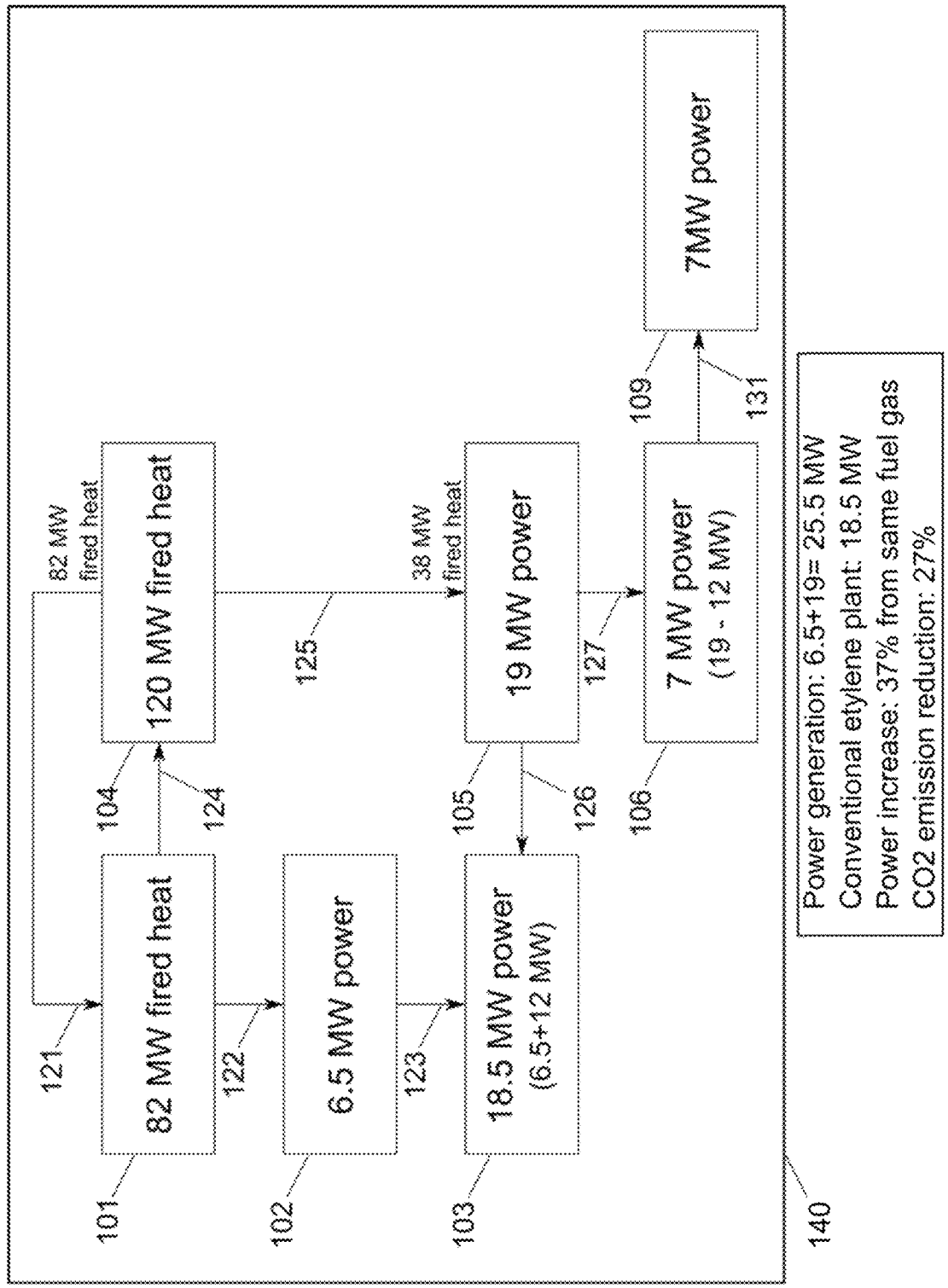
FIG. 4 shows results for overall power supplied/generated in a reference low emission ethylene plant, without methane storage (Example 1).

By using this arrangement, having a low emission cracking furnace at the heart of the plant, the fired heat is reduced by 31.87% from 120 MW (for a conventional furnace, see FIG. 3) to 82 MW and the power generated within the ethylene plant is reduced from 18.5 MW to 6.5 MW. This is shown by comparing the generation and consumption figures of fuel and power of FIG. 3 with those of FIG. 4, for the conventional ethylene plant circuit and for an ethylene plant arrangement having a low emission cracking furnace, respectively. This is achieved by raising the firebox efficiency of the cracking furnace from 40% to 53%. This means that the ethylene plant has a shortage of 12 MW power and an excess fuel gas production of 32%, as this fuel gas was previously fired on the cracking furnace.

By the integration of the cracking furnace with the power plant, it is possible to convert this excess fuel gas to power in the CCGT power plant at 50% heat-to-power efficiency instead of 32%, which is the heat-to-power efficiency in the ethylene plant as explained below. The saved fuel amounts to 38 MW heat (120-82 MW), as compared to a conventional ethylene plant system, where the cracking furnace firebox efficiency is 40%. In the latter situation, this converts to 12 MW power. This corresponds to a heat-to power conversion of a conventional ethylene plant system of 12/38=31.6%. It is possible to convert this excess fuel gas in the CCGT at 50% efficiency, resulting in 0.5*38 MW heat=19 MW power, of which 12 MW is delivered to the ethylene plant to compensate for the shortage discussed above and 7 MW power is available for export. These 12 MW can be delivered to the ethylene plant as electric power directly to an electro motor in order to drive a machine, but it can also be provided as high pressure steam in order to drive a machine via a steam turbine and supply this energy in the form of shaft power.

As the power generated is raised from 18.5 MW to 25.5 MW by the extra 7 MW raised in the CCGT, an extra 37% more power generation (duty) for the same amount of $CO_2$ produced, the reduction of the specific CO2 emission is 27%. This is 27% less $CO_2$ per MW of power produced. These extra 7 MW of power can be delivered as a continuous stream to the external grid.

Example 2 (Methane-Enriched Fuel Storage)

Figure 5:
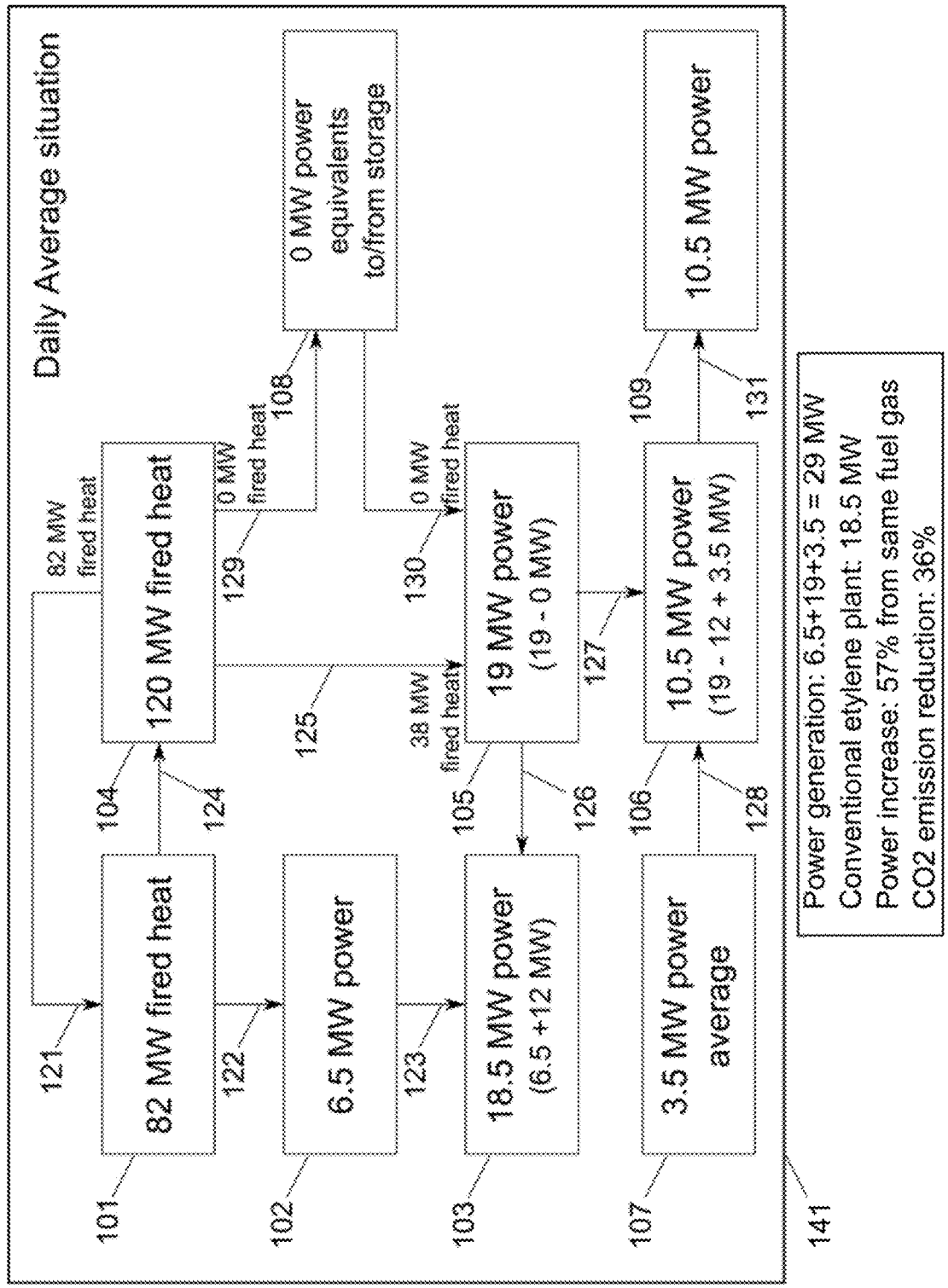
FIG. 5 shows results for overall power supplied/generated in an ethylene plant according to the invention in accordance with Example 2, without electrolyzer.

The arrangement of Example 1 is modified by including a liquefied methane storage, as schematically shown in FIGS. 1 and 5, for excess methane-enriched fuel separated from the cracked gas (FIG. 5 showing daily averaged generation and consumption figures of fuel and power).

By storing the excess fuel, the ethylene plant can be used to help the introduction of renewables to the power grid. One of the main issues to be dealt with is that it is difficult to handle the power fluctuations associated with renewable power sources. This invention solves that issue, by using the ethylene plant excess fuel production as back-up and convert it to power at high efficiency in a CCGT during periods that there is a renewable power deficit.

With an average supply of 3.5 MW renewable electric power, a peak supply of 10.5 MW and an availability of renewable power for 8 hours per day to the low emission integrated ethylene plant (the CCGT having 22.5 MW peak capacity and 19 MW base capacity) and a fuel storage capacity equivalent to 7 MW electric power (cf. the 7 MW electric power available for export in Example 1) the following improvements are feasible:
- a further raise in generated power to 29 MW (due to the extra 3.5 MW renewable power) (cf. 25.5 MW for the integrated arrangement of Example 1);
- a 50% increase in the power available for export to 10.5 MW on a continuous basis (cf. 7 MW in the integrated arrangement of Example 1);
- up to an extra 57% more power generation (duty) for the same amount of $CO_2$ produced (cf. 37% in the integrated arrangement of Example 1);
- up to 36% reduction of the specific $CO_2$ emission (cf. 27% reduction in the integrated plant of Example 1).

Compared to the integrated system of Example 1, an increase of up to 50% in exported power is feasible on a continuous basis. The fluctuations in the renewables are handled by the CCGT and the fuel storage. The load shift of the CCGT is from 40% to 120%, assuming a 19 MW base load.

In practice, one may operate away from the optimal operating point, whereby the CCGT won't operate at a heat-to-power efficiency of 50%. Then, the power output will be less than expected on the basis of a heat-to-power efficiency of 50%. Then, the increase of the power by 57% will be lower and the associated reduction in $CO_2$ emissions will also be lower than 36%, for instance about 30% or less, e.g. at about the same level as the integrated system of Example 1. Also in an embodiment wherein there is no further reduction of $CO_2$ emissions compared to the integrated system of Example 1, there will still be a reduction in $CO_2$ emissions compared to a conventional ethylene plant system, without methane storage and a CCGT for power generation, where the cracking furnace firebox efficiency is 40%, as is presented in FIG. 3.

Apart from benefits in $CO_2$ emission reduction, a major advantage of the ethylene plant according to the invention is being able to provide a stable production of power to the internal and external grid at essentially the same capacity level as the renewables power source's peak capacity, even with a poor availability factor of the renewable power source of only 33% (8 hours out of 24 hours) as has been taken in this example.

Figure 6:
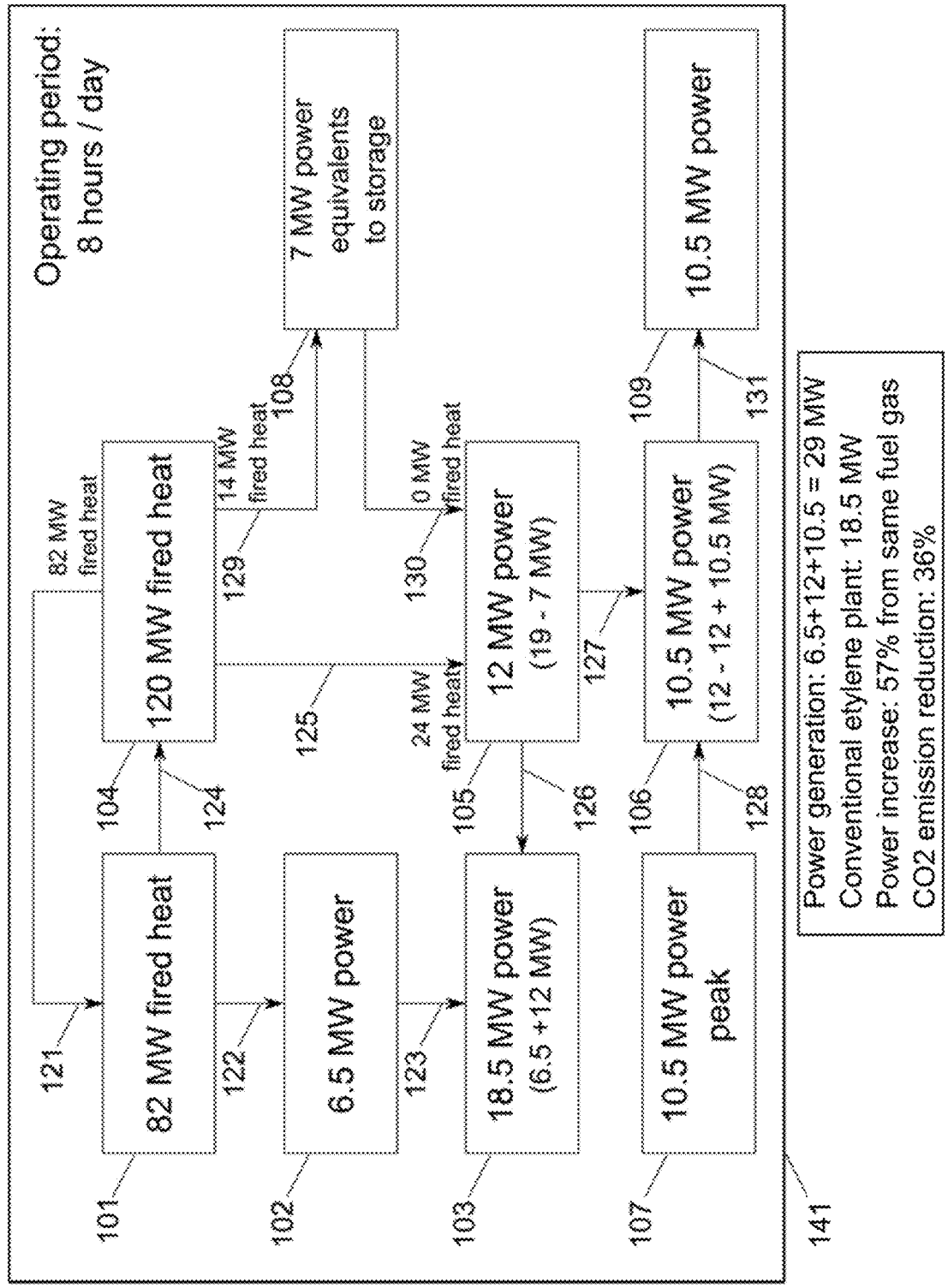
FIG. 6 shows results for power supplied/generated in accordance with Example 2, whilst renewable power is available.

As mentioned above and shown in FIG. 6, the arrangement is configured for a peak load of renewable energy of 10.5 MW. With a methane storage capacity it is possible to store the full production of excess fuel for 8 hours at a rate of 7 MW power equivalents. During this time, the CCGT power plant can run at a minimum load of 12 MW to produce the required power to operate the ethylene plant itself. So the ethylene plant's power demand limits the turn-down of the CCGT power plant. The fact that the CCGT can be run at a reasonable load at all times is another positive aspect of the invention.

Figure 7:
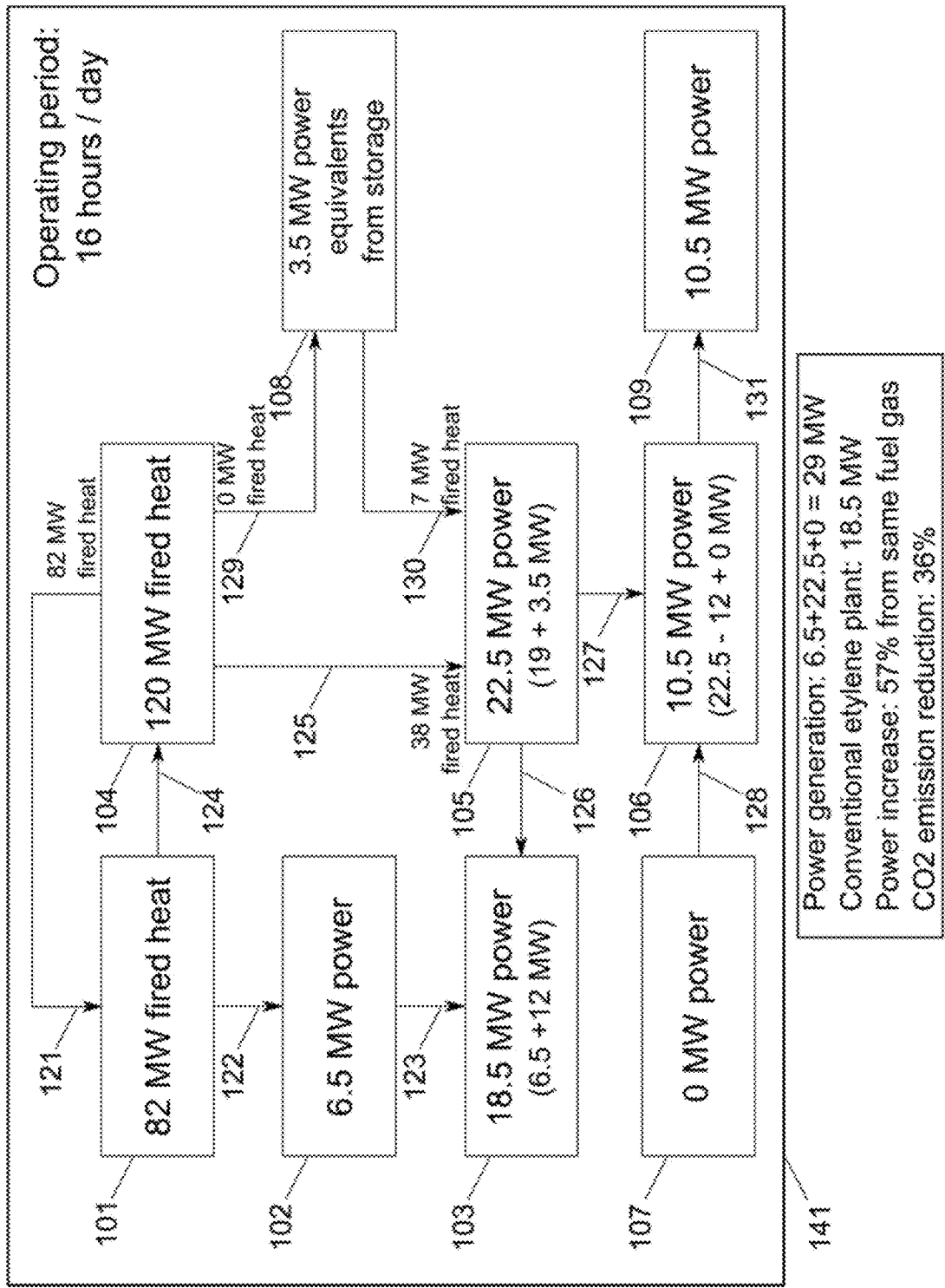
FIG. 7 shows results for power supplied/generated in accordance with Example 2, whilst renewable power is not available.

When there is no supply of renewable electric power (FIG. 7), excess fuel gas from storage is available to be delivered to the CCGT for 16 hours at a rate of 3.5 MW power equivalents, half of its full capacity over a period twice as long. During this time, the CCGT power plant can supply the 10.5 MW to the external grid and at the same time produce the 12 MW required to operate the ethylene plant, when running at a peak load of 22.5 MW (19 MW from excess fuel gas directly and 3.5 MW from fuel gas from the storage area).

Example 3 (Electrolyzer to Convert Renewable Power into Hydrogen-Rich Fuel)

Figure 8:
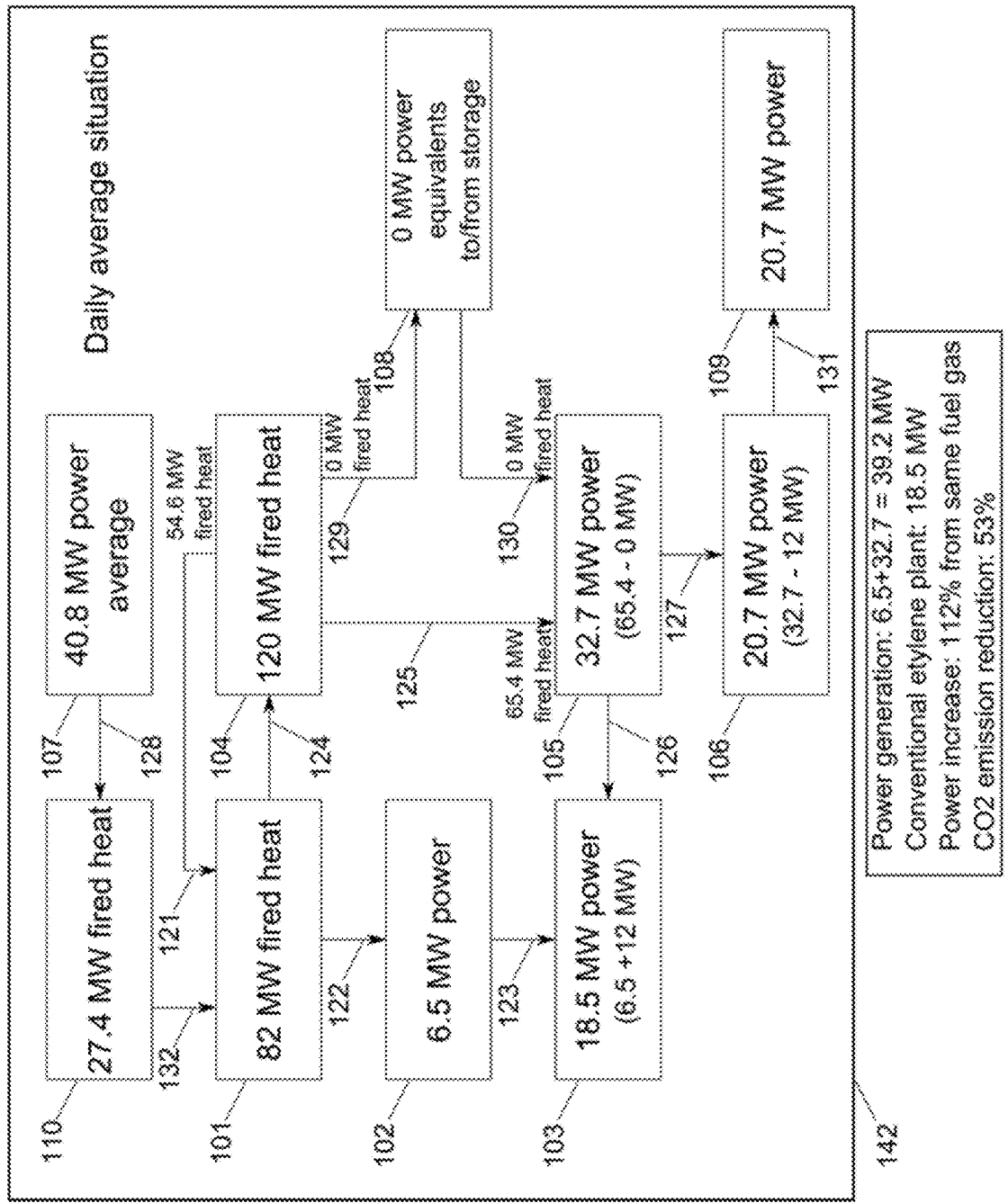
FIG. 8 shows results for overall power supplied/generated in an ethylene plant according to the invention in accordance with Example 3, with electrolyzer.

The arrangement of Example 2 is adapted to include an electrolyzer configured to produce hydrogen (and oxygen) from water and using renewable power (FIG. 8 showing daily averaged generation and consumption figures of fuel and power).

The electrolyzer requires nearly 1.5 MW electric power to generate 1.0 MW equivalents of hydrogen in terms of fired heat.

When operating 8 hours at peak load and 16 hours at no load, the peak load should be sufficient to replace all the fuel gas originally used for the high efficiency/low emission cracking furnace by hydrogen: The required quantity is 82 MW in terms of fired heat. The required renewable electric power is 82*1.49=122.5 MW. At peak load, all the excess fuel gas (even the 10 vol % hydrogen already present in this fuel gas, for simplicity) can thus be stored and/or used for power generation. This raises the fuel gas storage/availability for power generation with 82 MW heat to 120 MW heat, the same amount that is used by the cracking furnace before the modification to a low emission furnace (see FIG. 4). With a heat-to-power efficiency of the CCGT of 50%, this 82 MW heat can be converted to 41 MW of power. This on top of the 19 MW power provided in the integrated arrangement of Example 1. In this case, the complete fuel production of 120 MW heat can potentially be converted to 60 MW power in the CCGT (41+19=60).

Figure 9:
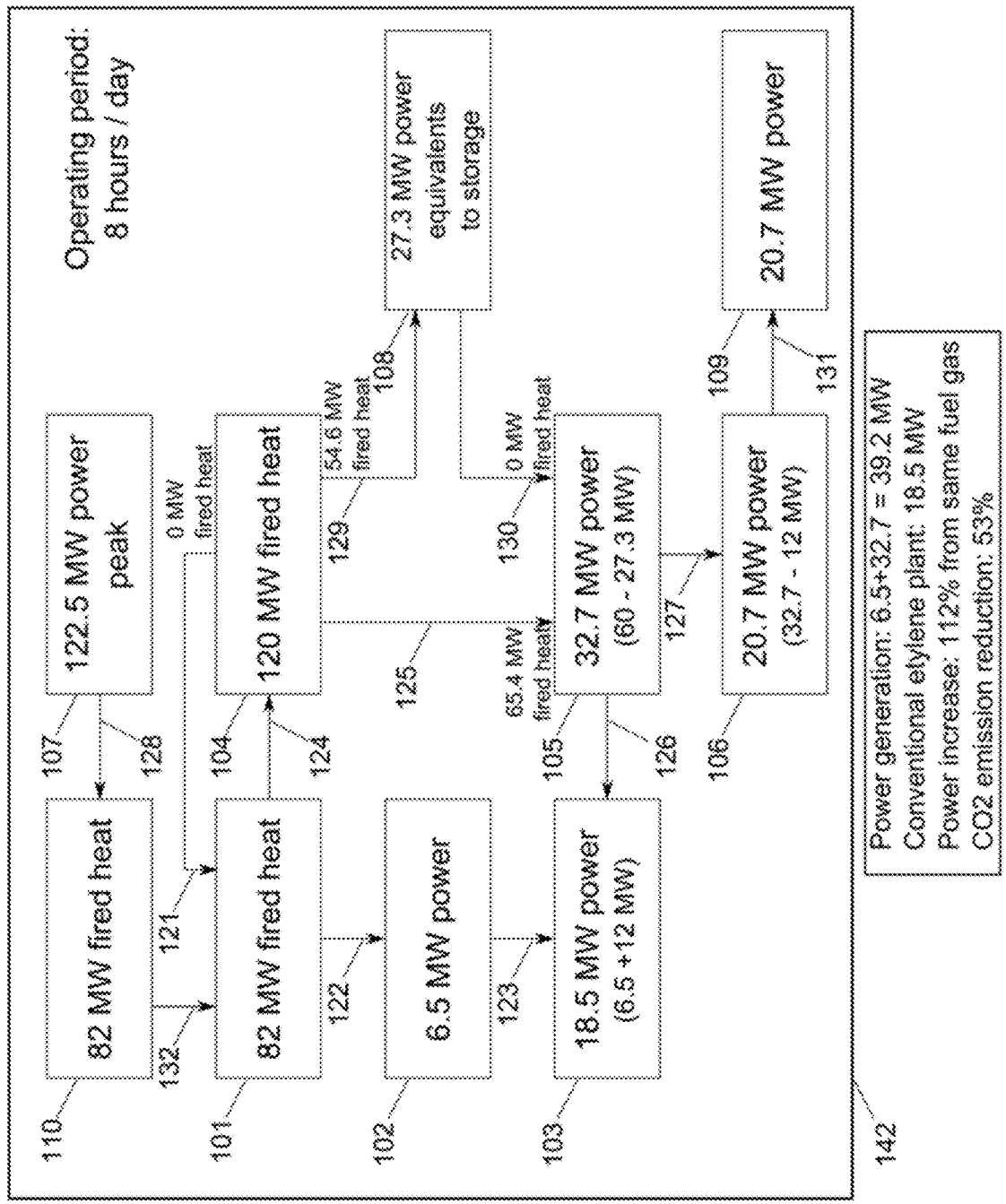
FIG. 9 shows results for power supplied/generated in accordance with Example 3, whilst renewable power is available.

During peak load the plant can deliver 20.7 MW power as is shown in FIG. 9. During this time, part of the production of excess fuel gas can be stored for 8 hours at a rate of 27.4 MW power equivalents. During this time, the CCGT power plant supplies 20.7 MW to the external grid, and at the same time produces the 12 MW required to operate the ethylene plant. In order to achieve this, at peak load the electrolyzer has to supply 82 MW equivalent fired heat to the furnaces. This corresponds to an electric power of approximately 122.5 MW.

Figure 10:
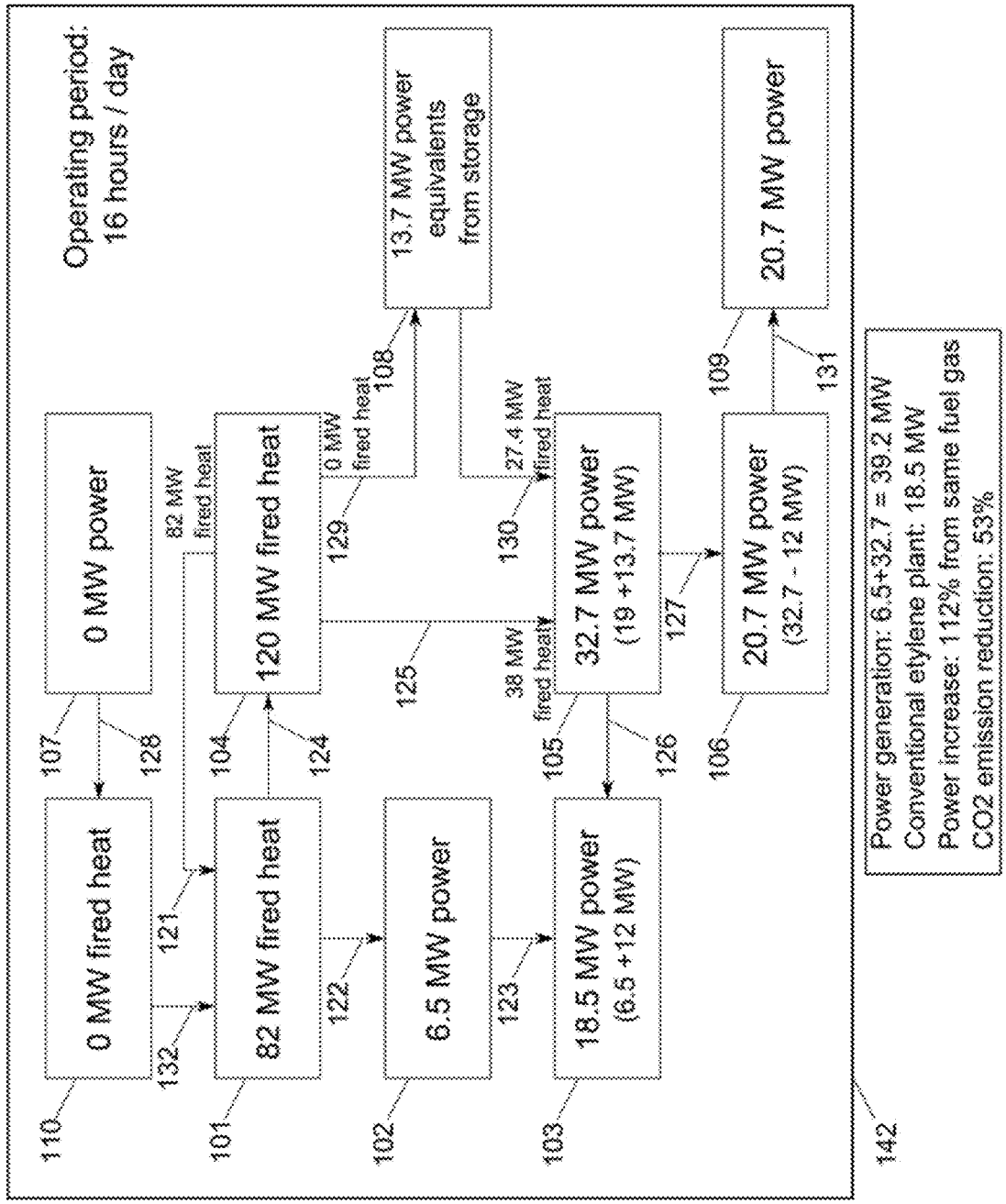
FIG. 10 shows results for power supplied/generated in accordance with Example 3, whilst renewable power is not available.

When there is no renewable electric power available (16 hrs per day in this example), no electric power nor hydrogen is provided (directly) from renewable sources (FIG. 10).

During this time, excess fuel gas from storage can be delivered to the CCGT for 16 hours at a rate of 13.7 MW power equivalents, half of the maximum storage capacity of 27.4 MW power equivalents over a period twice as long. During this time, the CCGT power plant produces the 12 MW required to operate the ethylene plant and generates a surplus of 20.7 MW which is exported to the external grid. Due to the storage, the CCGT power plant runs at the same load as during periods wherein renewable power is available at peak load: 32.7 MW (19 MW from excess fuel gas directly and 13.7 MW from fuel gas from the methane storage).

Compared to the integrated system of Example 2, a 100% increase of exported power is feasible on a continuous basis. The fluctuations in the renewables are handled by the CCGT and the fuel storage. The CCGT can on a continuous basis be run at its optimal design point of 32.7 MW. This operation allows the CCGT to operate essentially full-time at an optimum heat-to-power efficiency (50%).

A major advantage of this embodiment is being able to provide a stable production of power to the external grid at or close to its optimal design point. This means that the specific $CO_2$ emission level can be reduced in excess of 53%, without the need for carbon capturing, even with a poor availability of the renewable power of 33% (8 hours per day).

Compared to the embodiment of Example 2 (methane storage, but no electrolyzer), the continuous power produced from the renewable sources of 20.7 MW is nearly half of the average capacity of the renewable power produced of 40.8 MW; the main reason being that the production of 1 MW of hydrogen in terms of fired heat requires nearly 1.5 MW of electric power to be supplied. This has to do with the fact that the hydrogen and the oxygen produced are in the gas phase, while the water is in the liquid phase. In other words, in addition to splitting the molecule, the latent heat has to be supplied as well. The produced flue gas from the combustion of the hydrogen is not condensed, so the latent heat is not recovered. On the other hand, supplying hydrogen for use in vehicles would have an additional 0.4 MW associated with it. Nevertheless, this makes the hydrogen relatives expensive and its economical application will depend on the value of the $CO_2$ credits and the return of investment (ROI) percentage that is acceptable for these large and long-term investments associated with the renewables, the electrolyzers and the methane storage. Considering the life time of ethylene plants, the inventors expect that that lower ROI percentages are acceptable, when these additional equipment items (renewable power plant and electrolyzer) are implemented in accordance with the invention.

ACKNOWLEDGEMENTS

The work leading to this invention has received funding from the European Union Horizon H2020 Programme (H2020-SPIRE-04-2016) under grant agreement no 723706.

LEGEND TO FIGURES

1. Cracking furnace
2. Separation section
3. Methane storage
4. Methane evaporator
5. Gas turbine combustion chamber
6. Gas turbine
7. Combustion air compressor
8. Waste heat recovery boiler
9. Power plant steam turbine
10. Electric power generator
11. Ethylene plant steam turbine
12. Power plant surface condenser
13. Ethylene plant surface condenser
14. Boiler feed water pump
15. Power plant electric power generator or ethylene plant compressor
16. Ethylene plant compressor and/or pump
21. Hydrocarbon feedstock
22. Cracked gas
23a-23c. Hydrogen-enriched fuel
24a-24j. Methane-enriched fuel
25. Ethylene-enriched product
26. Air
27. Exhaust gas
28. Boiler feed water
29. High pressure steam
31. Internal power grid
32. External power grid
33. Renewable power source
41. Power output control system
42. Firing control system
43. Control valve
51. Integrated low emission ethylene and power plant with renewable power import
52. Integrated low emission ethylene and power plant with renewable power import and electrolyzer
61. Electrolyzer
62. Demineralized water
63a-63b. Hydrogen fuel
64. Oxygen
101. Cracking furnace
102. Ethylene plant power generation
103. Ethylene plant power users
104. Separation section
105. Combined Cycle Gas Turbine system
106. Internal grid
107. Renewable power source
108. Methane storage
109. External grid
110. Electrolyzer
121. Fuel
122. High pressure steam
123. Power from ethylene plant
124. Cracked gas
125. Excess methane-enriched fuel to CCGT
126. Power from CCGT to ethylene plant by electric power or high pressure steam
127. Power from CCGT to internal grid
128. Power from renewable sources
129. Excess methane-enriched fuel to storage
130. Excess methane-enriched fuel from storage
131. Power to external grid
132. Hydrogen fuel
139. Conventional ethylene plant
140. Integrated low emission ethylene and power plant
141. Integrated low emission ethylene and power plant with renewable power import
142. Integrated low emission ethylene and power plant with renewable power import and electrolyzer

The invention claimed is:

1. Ethylene plant, comprising:
a cracking furnace for converting a hydrocarbon feedstock into a cracked gas stream;
a separation section configured to provide at least an ethylene-enriched product stream, a hydrogen-enriched fuel stream and a methane-enriched fuel stream from the cracked gas stream;
a passage way for feeding at least part of the hydrogen-enriched fuel from the separation section to a burner of the cracking furnace and/or a passage way for feeding at least part of the hydrogen-enriched fuel from the separation section to a burner of a waste heat recovery boiler of a combined cycle gas turbine power plant (CCGT);
a methane storage configured for storing the methane-enriched fuel and a passage way for feeding at least part of the methane-enriched fuel from the separation section to the storage;
the CCGT, comprising a gas turbine—the gas turbine comprising a combustor—and a passage way for feeding at least part of the methane-enriched fuel from the storage to the combustor of the gas turbine of the CCGT, which CCGT is configured to generate electric power and/or to generate high pressure steam to drive a steam turbine forming part of a steam generation circuit of the ethylene plant; and
an electric power connection configured to provide part of the power for operating the plant, which is a connection to an electric power system to produce electric power from a renewable source.

2. Ethylene plant according to claim 1, wherein
the methane storage is configured for storing liquefied methane-enriched fuel, obtained directly from the separation section or after liquefying a gaseous methane-enriched fuel stream from the separation section, and
the passage way for feeding at least part of the methane-enriched fuel from the storage to the combustor of the gas turbine of the CCGT is configured to feed liquefied methane-enriched fuel to the combustor of the gas turbine of the CCGT via an evaporator unit configured to convert at least part of the liquefied methane-enriched fuel into a gaseous methane-enriched fuel.

3. Ethylene plant according to claim 1, wherein the separation section is further configured to separate a gaseous methane-enriched fuel stream from the cracked gas, the plant further comprising at least one of:
a passage way for feeding part of the gaseous methane-enriched fuel from the separation section to the burner of the cracking furnace; and
a passage way for feeding part of the gaseous methane-enriched fuel from the separation section to the burner of the waste heat recovery boiler of the CCGT.

4. Ethylene plant according to claim 1, wherein the passage way for feeding part of the methane-enriched fuel is configured for feeding liquefied methane-enriched fuel from the storage to the burner of the cracking furnace.

5. Ethylene plant according to claim 1, wherein the storage is configured for storing liquified methane-enriched fuel and the plant comprises a passage way for feeding part of the liquefied methane-enriched fuel from the storage to the burner of the waste heat recovery boiler of the CCGT via an evaporator unit configured to convert at least part of the liquefied methane-enriched fuel into a gaseous methane-enriched fuel.

6. Ethylene plant according to claim 1, comprising a controlling system configured to compensate for fluctuations in the electric power provided via the renewable electric power connection, wherein a fuel flow rate and/or pressure in one or more of said passage ways is regulated, in response to the (existing or expected) fluctuations thereby increasing electric power output of the CCGT when electric power provided by said electric power connection decreases or is expected to decrease and electric power output of the CCGT when electric power provided by said electric power connection increases or is expected to increase.

7. Ethylene plant according to claim 1, wherein the electric power system comprises a power system selected from the group consisting of wind power systems, solar energy systems, hydropower systems, geothermal energy systems, osmotic power systems, systems configured to generate electricity from biomass and systems configured to generate electricity from a bio-renewable fuel, e.g. bio-ethanol or biodiesel.

8. Ethylene plant according to claim 1, comprising an electrolyzer, wherein the electric power connection is connected to the electrolyzer, which electrolyzer is configured to use at least part of the electric power from the renewable source and to use at least part of the electric power generated by the CCGT to generate hydrogen by electrolysis, and further comprising a passage way for feeding generated hydrogen from the electrolyzer to the burner of the cracking furnace and/or a passage way for feeding generated hydrogen from the electrolyzer to the burner of the waste heat recovery boiler of the CCGT.

9. Ethylene plant according to claim 1, wherein the electric power system configured to produce electric power from a renewable source is an integrated part of the ethylene plant or an integrated part of an industrial complex of which the ethylene plant is a part and/or wherein the electric power system is connected to the ethylene plant via an external electricity grid.

10. Ethylene plant according to claim 9, wherein both said electric power system configured to produce electric power from a renewable source and the CCGT have an electric connection to an internal grid of the ethylene plant or industrial complex of which the ethylene plant is a part and wherein the ethylene plant further has an electric connection which electric connection is configured to allow receiving electric power from the power plant providing renewable electric power and to allow the supply of surplus power outside the ethylene plant.

11. Ethylene plant according to claim 1, having an ethylene plant steam generation circuit and a power plant circuit, the ethylene plant steam generation circuit comprising:
said cracking furnace, wherein the cracking furnace is configured to generate high pressure steam from boiler feed water;
a steam turbine configured to be driven by said high pressure steam;
a process compressor configured to be driven by the steam turbine;
a condenser configured to condense at least part of the high pressure steam;
a pump configured to pump the condensed steam to the cracking furnace as boiler feed water;
the power plant circuit comprising the waste heat recovery boiler configured to recover heat as high pressure steam,
wherein the system further comprises a first connection between the ethylene plant steam generation circuit and the power plant circuit configured to lead at least part of the high pressure steam from the waste heat recovery boiler to the at least one steam turbine of the ethylene plant steam generation circuit to drive said at least one steam turbine.

12. Ethylene plant according to claim 11, wherein the ethylene plant steam generation circuit includes a process compressor which is configured to be driven directly by the gas turbine of the power plant circuit.

13. Ethylene plant according to claim 11, wherein the power plant circuit further includes at least one steam turbine and at least one generator, wherein the circuit is configured to provide at least part of the high pressure steam from the waste heat recovery boiler to the at least one steam turbine of the power plant circuit, wherein the at least one steam turbine is configured to drive the at least one generator for generating power.

14. Ethylene plant according to claim 1, wherein the plant comprises a machine configured to be driven by electric power from the CCGT and/or by electric power from the electric power system configured to produce electric power from a renewable source.

15. Ethylene plant according to claim 1, wherein the cracking furnace is a high efficiency cracking furnace.

16. Ethylene plant according to claim 15, wherein the ethylene plant has an integrated ethylene and power plant system and the high efficiency cracking furnace includes a radiant section, a convection section and a cooling section, wherein the cooling section includes at least one transfer line exchanger configured to preheat feedstock before entry into the radiant section, and wherein a convection section comprises a boiler coil configured to generate saturated steam from flue gas, said boiler coil being located in a bottom part of the convection section.

17. Ethylene plant according to claim 16, wherein the convection section comprises a second high temperature coil configured to preheat feedstock after exit of the feedstock from the transfer line exchanger and before entry into the radiant section, said second high temperature coil being located in a bottom part of the convection section.

18. Ethylene plant according to claim 1, wherein said cracking furnace is a fired cracking furnace.

19. Ethylene plant according to claim 1, wherein said cracking furnace is a rotodynamic pyrolysis reactor and wherein the plant comprises said passage way for feeding at least part of the hydrogen-enriched fuel from the separation section to said burner of said waste heat recovery boiler of said combined cycle gas turbine power plant.

20. Ethylene plant according to claim 1, wherein said cracking furnace is an electrically heated cracking furnace and wherein the plant comprises said passage way for feeding at least part of the hydrogen-enriched fuel from the separation section to said burner of said waste heat recovery boiler of said combined cycle gas turbine power plant.

21. Ethylene plant according to claim 1, comprising a plurality of cracking furnaces selected from the group consisting of fired cracking furnaces, rotodynamic pyrolysis reactors and electrically heated cracking furnaces.

22. Process for producing ethylene from a hydrocarbon feed, comprising:
cracking the hydrocarbon in a cracking furnace of an ethylene plant to produce a cracked hydrocarbon-containing gas, comprising ethylene, hydrogen and methane;
separating at least part of the cracked hydrocarbon-containing gas at least into an ethylene-enriched product, a hydrogen-enriched fuel and a methane-enriched fuel;
feeding at least part of the hydrogen-enriched fuel from a separation section to a burner of the cracking furnace and/or feeding at least part of the hydrogen-enriched fuel from the separation section to a burner of a waste heat recovery boiler of a combined cycle gas turbine power plant (CCGT);
feeding at least part of the methane-enriched fuel, obtained directly from the separation section as a liquid or after liquefying a gaseous methane-enriched fuel stream from the separation section, to a methane storage;
feeding at least part of the methane-enriched fuel from the storage to the combustor of the CCGT wherein said methane-enriched fuel from the storage is vaporized before it is fed into the combustor; and
subjecting the vaporized methane-enriched fuel fed to a combustor of the CCGT, to combustion in the CCGT, thereby generating electric power and/or thereby generating high pressure steam for driving a steam turbine forming part of a steam generation circuit of the ethylene plant,
wherein at least a part of the power is electric power produced from a renewable source.

23. Process according to claim 22, wherein from the cracked gas further a gaseous methane-enriched stream is obtained and at least a part of the gaseous methane-enriched fuel is fed from the separation section to the burner of the cracking furnace without having been subjected to a liquefying step and/or at least a part of the gaseous methane-enriched fuel is fed from the separation section to the burner of the waste heat recovery boiler of the CCGT without having been subjected to a liquefying step, wherein a part of the liquefied methane-enriched fuel is fed from the methane storage to a burner of the cracking furnace, said methane-enriched fuel from the storage having been vaporized before it is fed into the burner as a gas.

24. Process according to claim 23, wherein at least a part of the liquefied methane-enriched fuel is fed from the methane storage to the burner of the cracking furnace and/or to the burner of the waste heat recovery boiler of the CCGT, said methane-enriched fuel from the storage having been vaporized before it is fed into the burner of the cracking furnace as a gas.

25. Process according claim 22, wherein fluctuations in the electric power produced from the renewable source provided via an electric power connection are compensated for by increasing the electric power output of the CCGT when electric power provided by said electric power connection decreases or is expected to decrease and decreasing electric power output of the CCGT when electric power provided by said electric power connection increases or is expected to increase.

26. Process according to claim 22, wherein water is electrolyzed to produce hydrogen by an electrolyzer as part of the ethylene plant using an electric power connection providing renewable electric power that is connected to the electrolyzer, and wherein at least part of the renewable electric power and at least part of the electric power generated by the CCGT is used by the electrolyzer to generate said hydrogen by electrolysis and at least part of the generated hydrogen is fed from the electrolyzer to the burner of the cracking furnace and/or the burner of a waste heat recovery boiler of the CCGT.

27. Process according to claim 22, wherein the cracking furnace is a rotodynamic pyrolysis reactor or an electrically heated cracking reactor and at least part of the hydrogen-enriched fuel is fed from the separation section to said burner of said waste heat recovery boiler of said combined cycle gas turbine power plant.

28. Process according to claim 22, wherein the cracking furnace is a fired cracking furnace comprising a firebox wherein one or more burners are present combusting fuel.

29. Process according to claim 22, wherein the ethylene plant is used for the temporary storage of renewable power.

30. Process according to claim 22, wherein the ethylene plant is used for the indirect conversion of hydrogen to methane-rich gas.

* * * * *